United States Patent [19]

Varma et al.

[11] Patent Number: 5,175,266

[45] Date of Patent: Dec. 29, 1992

[54] NUCLEOSIDES AND OLIGONUCLEOSIDES WITH A PHOSPHATE-FREE INTERNUCLEOSIDE BACKBONE AND PROCESS FOR PREPARING THE SAME

[75] Inventors: Rajender S. Varma; Michael E. Hogan; Ganapathi R. Revankar; Takkellapati S. Rao, all of The Woodlands, Tex.

[73] Assignees: Triplex Pharmaceutical Corporation, Houston, Tex.; Baylor College of Medicine, Houston, Tex.

[21] Appl. No.: 687,807

[22] Filed: Apr. 19, 1991

[51] Int. Cl.$^5$ ............... C07H 19/00; C07H 21/00; C07D 307/02
[52] U.S. Cl. ........................... 536/22; 549/499
[58] Field of Search ............... 536/22; 549/499

[56] References Cited

U.S. PATENT DOCUMENTS

| | | | |
|---|---|---|---|
| 4,625,065 | 11/1986 | Heather | 568/27 |
| 4,736,036 | 4/1988 | Mathiaparanam | 546/320 |
| 4,889,952 | 12/1989 | Shimizu et al. | 560/52 |

OTHER PUBLICATIONS

Singh et al "Ruthenium Tetraoxide: A Mild Reagent for the Oxidation of 2', 3'-O-Isopropylidene Purine Nucleosides" Tetrahedron Letters 33:237–240 (1992).

Primary Examiner—Nathan M. Nutter
Attorney, Agent, or Firm—Fulbright & Jaworski

[57] ABSTRACT

Nucleoside derivatives which contain a nucleo-base, a sugar and an amino acid backbone of the structure:

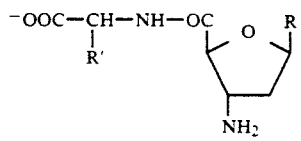

where R' refers to the various amino acid side chains or their blocked equivalent and R refers to a nucleo-base or its blocked equivalent. The synthesis of these nucleoside derivatives proceeds by a series of steps including oxidation of the 3'-azido nucleoside derivative, coupling to a benzylated ester of an amino acid to yield the amide and hydrogenation. The adenine, guanine, cytosine and thymine nucleosides with an amino acid at the 5' terminus are synthesized. From such monomers oligonucleotides can be synthesized which possess an amino acid backbone, using either solid state phase chemistry or liquid phase chemistry.

3 Claims, 13 Drawing Sheets

NUCLEOSIDES AND OLIGONUCLEOSIDES WITH A PHOSPHATE-FREE INTERNUCLEOSIDE BACKBONE AND PROCESS FOR PREPARING THE SAME

FIELD OF THE INVENTION

This invention relates to the field of phosphate-free nucleosides and the synthesis of phosphate-free nucleosides which are useful in the formation of oligonucleosides capable of forming a duplex or a triplex with a double stranded DNA.

BACKGROUND

Because of their capacity to base pair, oligonucleotides are used widely as diagnostic reagents and as tools in molecular genetics. More recently "antisense" oligonucleotides have been shown to block the translation and perhaps transcription of genes and are now actively investigated as a new class of pharmaceuticals.

A number of alternative phosphate-containing linkages are known to exist in the literature. A great deal of effort has been directed toward the synthesis of oligonucleotide analogues with an altered phosphodiester linkage to improve cellular uptake and to decrease the rate of degradation of oligonucleotides by nucleases which cleave the phosphodiester linkage. Thus far, the most extensively studied analogues have contained modified phosphate linkages. These analogues include oligonucleotide alkylphosphotriesters, oligonucleotide methylphosphonates, oligonucleotidephosphorothioatesand oligonucleotide alkylphosphoramidates. In most of these compounds, the linkage consists of a pair of diastereoisomers which have not been separated. Consequently, an oligomer having n non-ionic internucleotide linkages will consist of a mixture of $2^n$ isomers.

Other approaches to altering the backbone of oligonucleotides which are capable of forming a duplex or triplex include modifying the backbone. In these approaches the bridging phosphate group is replaced with other functional groups including carbonate, oxyacetamide, carbamate, silyl and ribonucleoside derived morpholino subunits linked by carbamate groups. However, these phosphate-free backbones are relatively unstable with respect to hydrolysis, are relatively insoluble in water and form duplexes which appear to differ from that of the natural oligonucleotides. All of the above phosphate analogues and non-phosphate derivatives have a variety of problems in terms of uptake into the cell, attack by or lack of attack by nucleases, insolubility in aqueous solution, binding and relative stability of binding for duplex and triplex formation. The present invention provides an improved method to synthesize chemical compounds capable of forming double helix or triplex-forming oligonucleotides. These chemical compounds exhibit chemical characteristics necessary to form a duplex or triplex, yet replace the phosphodiester linkage of the oligonucleotide backbone. The present invention provides a novel class of compounds capable of entering the cell, resisting nuclease attack and forming stable triplex structures.

SUMMARY OF THE INVENTION

An object of the present invention is a method for synthesizing novel phosphate-free nucleosides and oligonucleosides capable of forming duplexes or triplexes.

An additional object of the present invention is a method for making synthetic nucleosides and oligonucleosides which form duplexes or triplexes with DNA.

An additional object of the present invention is a novel synthetic method for forming an oligonucleoside containing a nucleic acid base, sugar and amino acid linker.

Another object of the present invention is the formation of a nucleoside and oligonucleoside having an amino acid backbone and capable of forming a duplex or triplex with duplex DNA.

Thus, in accomplishing the foregoing objects, there is provided in accordance with one aspect of the present invention a compound for the synthesis of nucleosides containing a nucleo-base, a sugar and an amino acid, having the structure

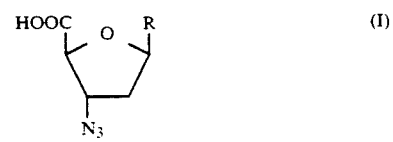

wherein R is nucleo-base.

A further aspect of the present invention is a method of synthesizing compound (I) comprising the steps of oxidizing a 5'-hydroxymethyl functionality of 3'-azido-2',3'-dideoxyribonucleoside or a 3'-azido-3'deoxyribonucleoside at ambient temperatures in the presence of ruthenium tetroxide.

In the preferred embodiments, the ruthenium tetroxide is generated in situ by treating $RuCl_3$ in an aqueous KOH solution with oxidizing agents selected from the group consisting of persulfate and periodates. Especially effective oxidizing agents have included to be $K_2S_2O_8$ and $NaIO_4$.

An additional embodiment of the present invention is an alternate method of synthesizing compound (I) comprising the steps of treating a pyrimidine 2,3' anhydronucleoside with ruthenium tetroxide to form a carboxylic acid derivative and warming the carboxylic derivative with lithium azide in dimethylacetamide.

Another aspect of the present invention is a method of synthesizing a nucleoside comprised of a nucleic acid base, a sugar and an amino acid comprising the steps of coupling compound (I) to a benzyl ester of an amino acid in anhydrous dimethylformamide and 1-ethyl-3-[3-(dimethylaminopropyl)]carbodiimide hydrochloride in the presence of triethylamine and subsequent catalytic hydrogenation (Pd/C) of an ethanolic solution of the coupled product.

In other embodiments, the ester of compound (I), the homopolymer of the nucleoside and mixed oligonucleosides of the nucleosides are synthesized.

Further embodiments include methods of synthesizing a dithioester of the following structure:

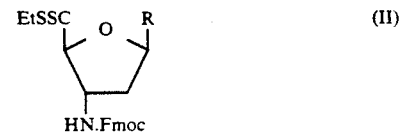

wherein R is a nucleo-base, comprising the steps of catalytic hydrogenation of compound (I), treatment with 9-fluorenylmethyl chloroformate under alkaline conditions and conversion to dithioester with 2,4-bis(ethylthio)-2,4-dithioxocyclo-di-$\lambda^5$-phosphathiane.

Also described are solid phase synthesis procedures for making polymeric nucleosides.

In alternate embodiments, the internucleoside backbone linkage includes a D- or L- amino acid. The amino acid is selected from a group consisting of glycine, aspartic acid, glutamic acid, serine, threonine, histidine, arginine, lysine, cysteine, methionine and phosphoserine. In the preferred embodiment, glycine or lysine are used.

Other and further objects, features and advantages will be apparent and eventually more readily understood from a reading of the following specification and by reference to the accompanying drawings, forming a part thereof, where examples of the presently preferred embodiments of the invention are given for the purpose of disclosure.

Figure 1:
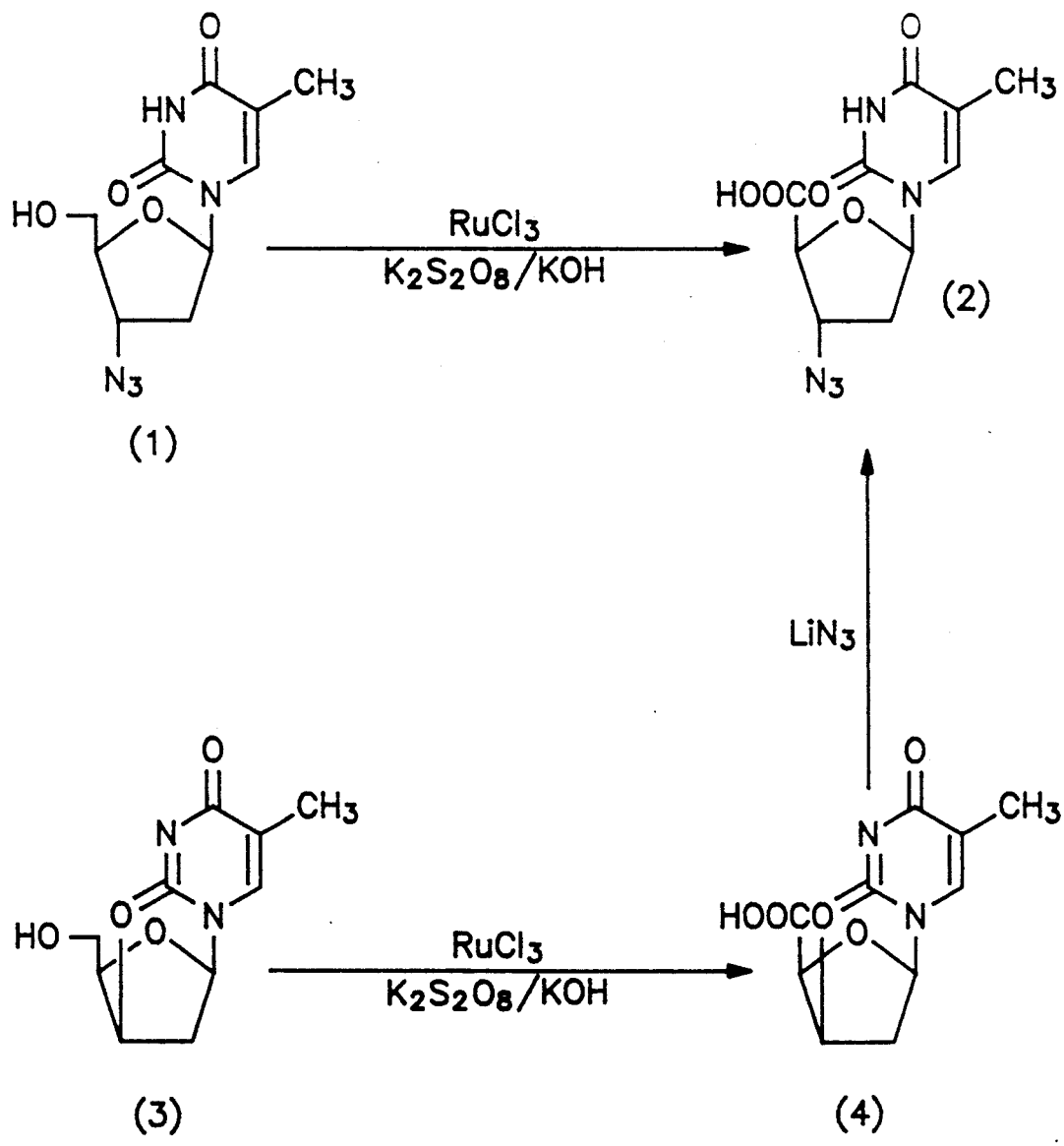
FIG. 1 is a schematic representation showing two alternate synthesis for the nucleoside precusser (I).

The drawings and figures are not necessarily to scale and certain features mentioned may be exaggerated in scale or shown in schematic form in the interest of clarity and conciseness.

DETAILED DESCRIPTION OF THE INVENTION

It will be readily apparent to one skilled in the art that various substitutions and modifications may be made to the invention disclosed herein without departing from the scope and the spirit of the invention.

The term "synthetic oligonucleosides" as used herein is defined as a molecule comprising two or more deoxyribonucleosides or ribonucleosides preferably more than 10. The exact size will depend on many factors including the specificity and binding affinity. The oligonucleoside will be comprised of a nucleo-base, a sugar and an amino acid.

As used herein, the term "coupling reagent" refers to those reagents which are used for coupling in peptide synthesis. Examples of coupling reagents include two types. Those which act by themselves, for example thionyl chloride, triethylamine-borane, or catecholborane. The second group of coupling reagents work with a helper compound like N-hydroxysuccinimide, N-hydroxysulfosuccinimide, and 1-hydroxybenzotriazole (HOBT) in N,N-dimethylformamide. Some examples of the coupling reagents in this latter class include dicyclohexylcarbodiimide (DCC), 1-ethyl-3-[3-(dimethylamino)propyl]carbodiimide chloride (EDC), Benzotriazole-1-yl-oxy-tris(dimethylamino)phosphonium hexafluorophosphate (BOP), O-Benzotriazol-1-yl-N,N,N',N'-tetramethyl-uronium hexafluoroshosphate (HBTU), O-(N-succinimidyl)-N,N,N',N'-tetramethyluronium tetrafluoroborate (TSTU). One skilled in the art will readily recognize that these compounds are only examples of coupling reagents and that other compounds are available to those skilled in the art.

When referring to bases herein the term includes both deoxyribonucleic acids and ribonucleic acids. The following abbreviations have been used: "A" refers to adenine as well as its derivatives, "T" refers to thymine as well as its derivatives, "G" refers to guanine as well as its derivatives, "C" refers to cytosine as well as its derivatives, "X" refers to xanthine as well as its derivatives and "I" refers to inosine as well as its derivatives.

As used herein the term "major groove" refers to one of the grooves along the outer surface of the DNA helix which is formed because the sugar phosphate backbone of the duplex DNA extends further from the axis than the bases do. The major groove is important for binding of regulator molecules to specific DNA sequences.

The term "TFO" or "triplex forming oligonucleoside" as used herein refers to the synthetic oligonucleosides of the present invention which are capable of forming a triplex by binding to the major groove of a duplex DNA structure.

Similarly, the term "DFO" or "duplex forming oligonucleoside" refers to synthetic oligonucleosides of the present invention which are capable of forming a duplex by binding to their Watson-Crick complement so as to form an anti-parallel double helix.

The term "internucleoside linkage" as used herein refers to the sugar, amino acid backbone linkage between the bases in the synthetic oligonucleoside. It replaces the internucleotide sugar phosphate linkages found in naturally occurring strands of DNA. In the present invention the internucleoside backbone linkage includes a D- or L-amino acid. The amino acid is selected from the group consisting of glycine, aspartic acid, glutamic acid, serine, threonine, histidine, arginine, lysine, cysteine, methionine and phosphoserine.

In order to make a TFO or DFO it is required that the oligonucleoside have the following characteristics:

1. The oligonucleoside backbone must provide sufficient conformational freedom to allow for base pairing and base overlap. In the naturally occurring phosphodiester backbone there is substantial conformational freedom in the duplex as determined by crystallographic order parameters, dynamics analysis and binding of intercalators. This conformational freedom is limited but finite. Thus, the alternative nucleoside linkage must provide for conformational flexibility similar to the five rotatable bonds which comprise the linkage between C-4' and C-3" in a duplex. The molecules of the present invention have about 5 to 7 rotatable bonds in the backbone linkage.

2. The charge is important. From a thermodynamic perspective, the anionic nature of the phosphodiester is intrinsically unfavorable. Upon duplex or triplex formation the anionic nature results in a very high local charge density in a duplex or triplex. Consequently, duplex or triplex formation is greatly destabilized in the absence of monovalent or divalent counterions. These counterions are consumed upon duplex or triplex formation and serve to shield closely spaced negative charge. Although the oligonucleosides of the present invention work when there is a negative charge or a positive charge or the molecule is neutral, in the preferred embodiment, a positive charged or neutral backbone is used.

3. Another important aspect of the phosphodiester linkage is the hydration. In general, macromolecules fold in aqueous solution so as to isolate water insoluble substituents from solution contact while presenting well hydrated substituents near the surface area in contact with water. This general principal is well known for protein folding, and is of equal importance to understanding a nucleic acid structure. Upon esterification of the 5'- and 3'- hydroxyl groups, deoxyribonucleosides become relatively water insoluble. This situation also pertains to oligonucleotides. Therefore, not surprisingly, DNA structures fold to minimize hydration of the nucleoside moiety and tend to form stacked arrays which minimize base contact with water. At the same time the nucleoside moiety provides tight surface binding of 6-8 $H_2O$ molecules and weaker binding of 10-15 $H_2O$ equivalents per nucleoside. This binding is principally in the major and minor grooves. In the preferred embodiment, the internucleoside linkage of the present invention is strongly hydrated to present a hydrophilic face to aqueous solution.

4. The oligonucleosides of the present invention are designed to be used for duplex forming (antisense) or triplex-forming pharmaceuticals. Thus, the internucleoside linkage must be stable with respect to general base catalysis and enzyme catalyzed hydrolysis in serum or cells.

5. Another characteristic of the novel nucleosides of the present invention is their ability to be adaptable to solid phase synthetic methods. The ability of the synthetic chemistry to be adapted to the solid phase synthetic methods facilitates the rapid production of the compounds.

In confirmation with the above characteristics one embodiment of the present invention includes as a composition of matter an oligonucleoside characterized as having a phosphate-free internucleoside backbone linkage; having about 5 to 7 rotatable bonds in said backbone linkage having a strongly hydrated internucleoside linkage presenting a hydrophilic face to aqueous solution; and capable of forming double or triple helices. In the preferred embodiment this composition of matter can be further characterized as having a positive charged or a neutral backbone. The oligonucleoside is further characterized as having considerable stability to general base catalysis or enzyme hydrolysis in body tissue. In one embodiment the internucleoside backbone linkage includes a D- or L-amino acid. The amino acid is usually selected from the group consisting of glycine, aspartic acid, glutamic acid, serine, threonine, histidine, arginine, lysine, cysteine, methionine and phosphoserine. In the preferred embodiment the amino acid is glycine or lysine.

Another embodiment of the present invention includes a compound for the synthesis of nucleosides containing a nucleo-base, a sugar and an amino acid said compound having the structure:

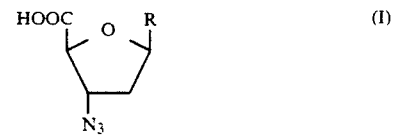

wherein R is a nucleo-base.

A further embodiment includes a method of synthesizing compound (I) comprising the step of oxidizing a 5'-hydroxymethyl functionality of a 3'-azido, 2',3'-dideoxynucleoside or a 3'-azido-3'-deoxynucleoside at ambient temperature in the presence of ruthenium tetroxide. (see FIG. 1).

In this method, the ruthenium tetroxide can be generated in situ by treating $RuCl_3$ in an aqueous KOH solution with oxidizing agents selected from the group consisting of persulfate and periodates. In the preferred embodiment, the oxidizing agents are either $K_2S_2O_8$ or $NaIO_4$.

An alternate method of synthesizing compound (I) comprises the steps of treating a pyrimidine 2,3'-anhydronucleoside with ruthenium tetroxide to form a carboxylic acid derivative and warming the carboxylic derivative with lithium azide and dimethylacetamide. (see FIG. 1).

A further embodiment of the present invention is a method of synthesizing a nucleoside comprising a nucleobase, a sugar and an amino acid by the steps of coupling compound (I) to a benzyl ester of an amino acid with a coupling reagent (for example, anhydrous dimethylformamide and 1-ethyl-3-[3-(dimethylaminopropyl)]carbodiimide hydrochloride in the presence of triethylamine) and subsequent catalytic hydrogenation (Pd/C) of an ethanolic solution of the coupled product. (see FIG. 2).

To help facilitate the coupling reaction in the nucleoside synthesis method, a compound selected from the group consisting of 1-hydroxybenzotriazole, N-hydroxysuccinimide and N-hydroxysulfosuccinimide can be added.

A polymer of the synthesized monomer nucleosides can be made by the steps of coupling the monomers to each other in anhydrous N,N-dimethylformamide with a coupling reagent (for example, dicyclohexylcarbodiimide) and a compound selected from the group consisting of 1-hydroxybenzotriazole, N-hydroxysuccinimide and N-hydroxysulfosuccinimide. A further improvement of this synthetic method is the addition of a step to remove the solvent and adding methanol to precipitate a water soluble polymer. This polymer can be used as a TFO or a DFO.

A variety of nucleoside carboxylic acids can be used in the above described nucleoside synthesis method. For example, in FIG. 2 the synthesis of thymidine conjugate is shown. When thymidine was used, the benzyl ester of an amino acid with appropriate amino acid side chain protection was selected from the group consisting of serine benzyl ester, $\epsilon$-acetyl lysine benzyl ester, glycine benzyl ester, threonine benzyl ester, aspartate benzyl ester, glutamate benzyl ester, histidine benzyl ester, methionine benzyl ester, cysteine benzyl ester and arginine benzyl ester.

When the nucleo-base in the nucleoside synthesis method is adenine, cytosine or guanine, it was found that a further step enhanced the reaction. (see FIGS. 6 and 7). Prior to the coupling step there is sequential protection first of the carboxylic functionality with t-butyldimethylsilyl and then the amine functionality with isobutyrylchloride or benzoyl chloride. The carboxylic functionality is then selectively deprotected with fluoride ion and the method proceeds as described above. The homopolymer of the nucleoside can be synthesized by coupling the synthesized monomers to each other with a coupling reagent (for example, dicyclohexylcarbodiimide and 1-hydroxybenzotriazole in anhydrous N,N-dimethylformamide) and deprotecting the polymer thus formed (see FIGS. 2, 6 and 7).

A further aspect of the present invention is the preparation of a compound of the structure:

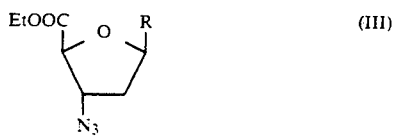
(III)

wherein R is a nucleo-base. The method comprises the steps of esterification of compound (I) with ethanol in the presence of dicyclohexylcarbodiimide and 4-dimethylaminopyridine (DMAP) or with ethanolic HCl in triethyl orthoformate. (see FIG. 3).

A further procedure is a method of synthesizing a dithioester of the formula:

(II)

wherein R as a nucleo-base. This compound can be synthesized by the steps of catalytic hydrogenation of compound (I) with Pd/C, treatment with 9-fluorenylmethyl chloroformate under alkaline conditions to give compound (11) which is further converted to the dithioester (10) with 2,4-bis(ethylthio)-2,4-dithioxocyclo-di-$\lambda^5$-phosphathiane (see FIG. 4).

Figure 4A:
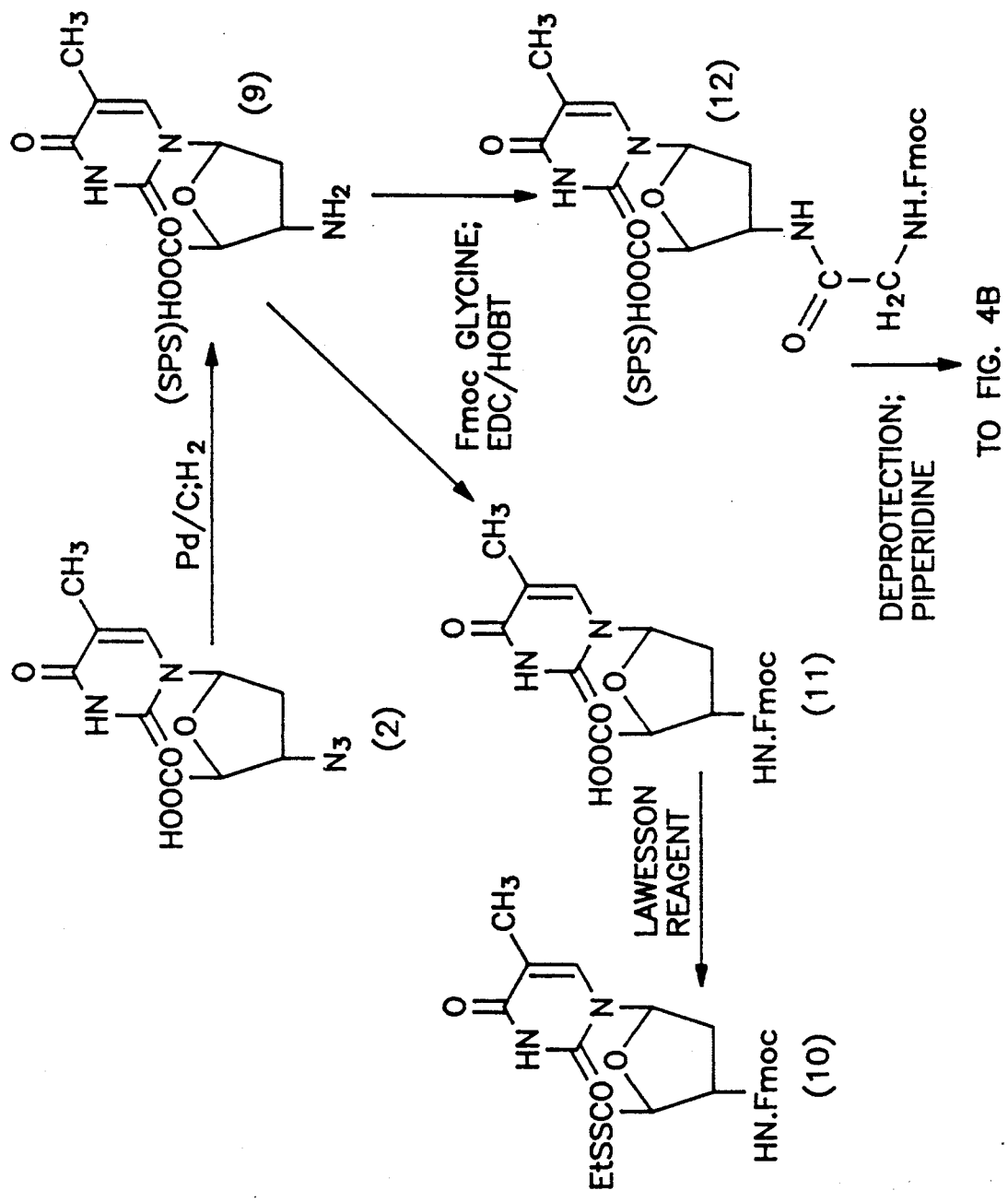
FIGS. 4A and 4B are schematic representation of a solid phase synthesis of oligonucleosides with an amino acid backbone.
Figure 4B:
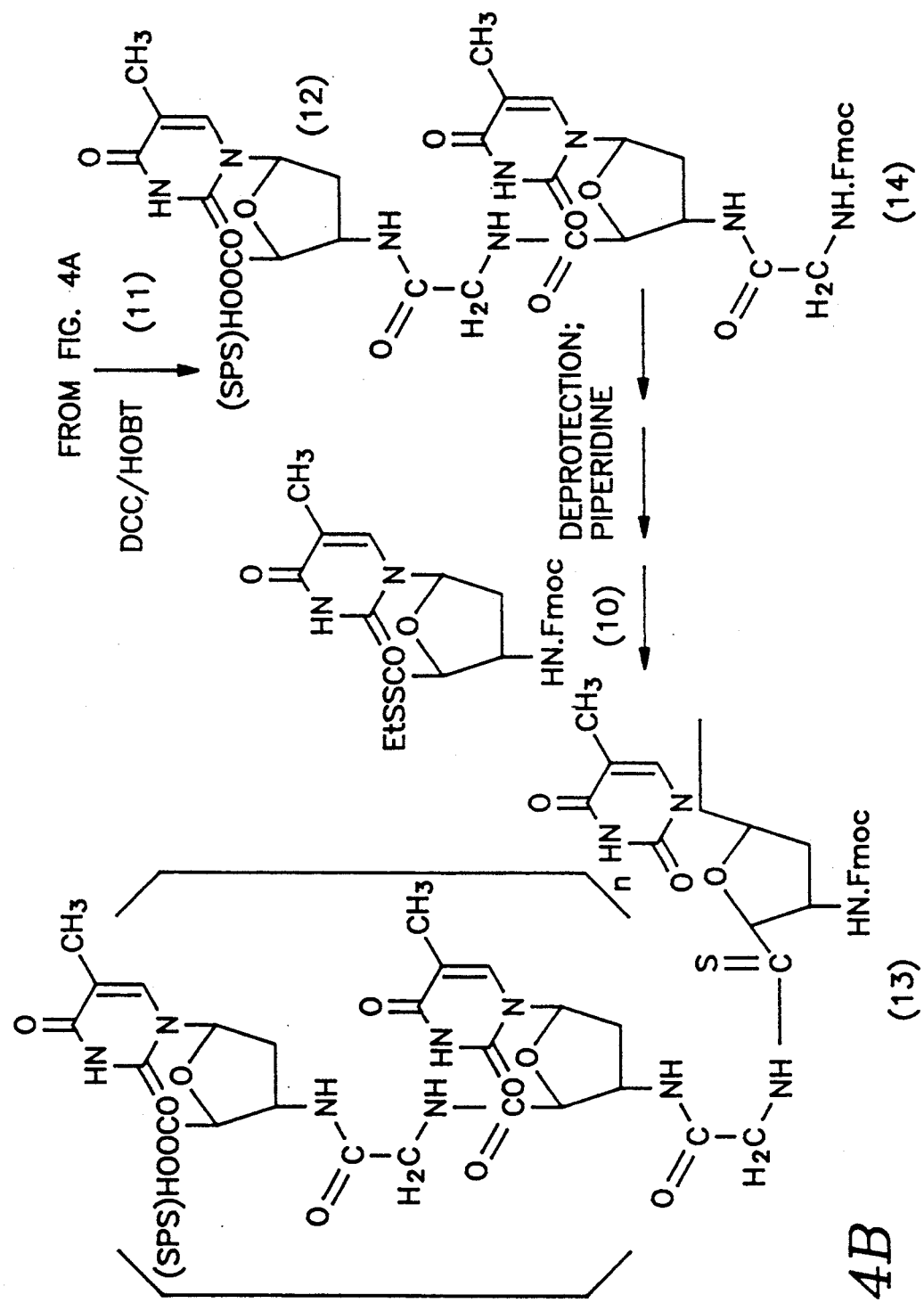
Figure 5:
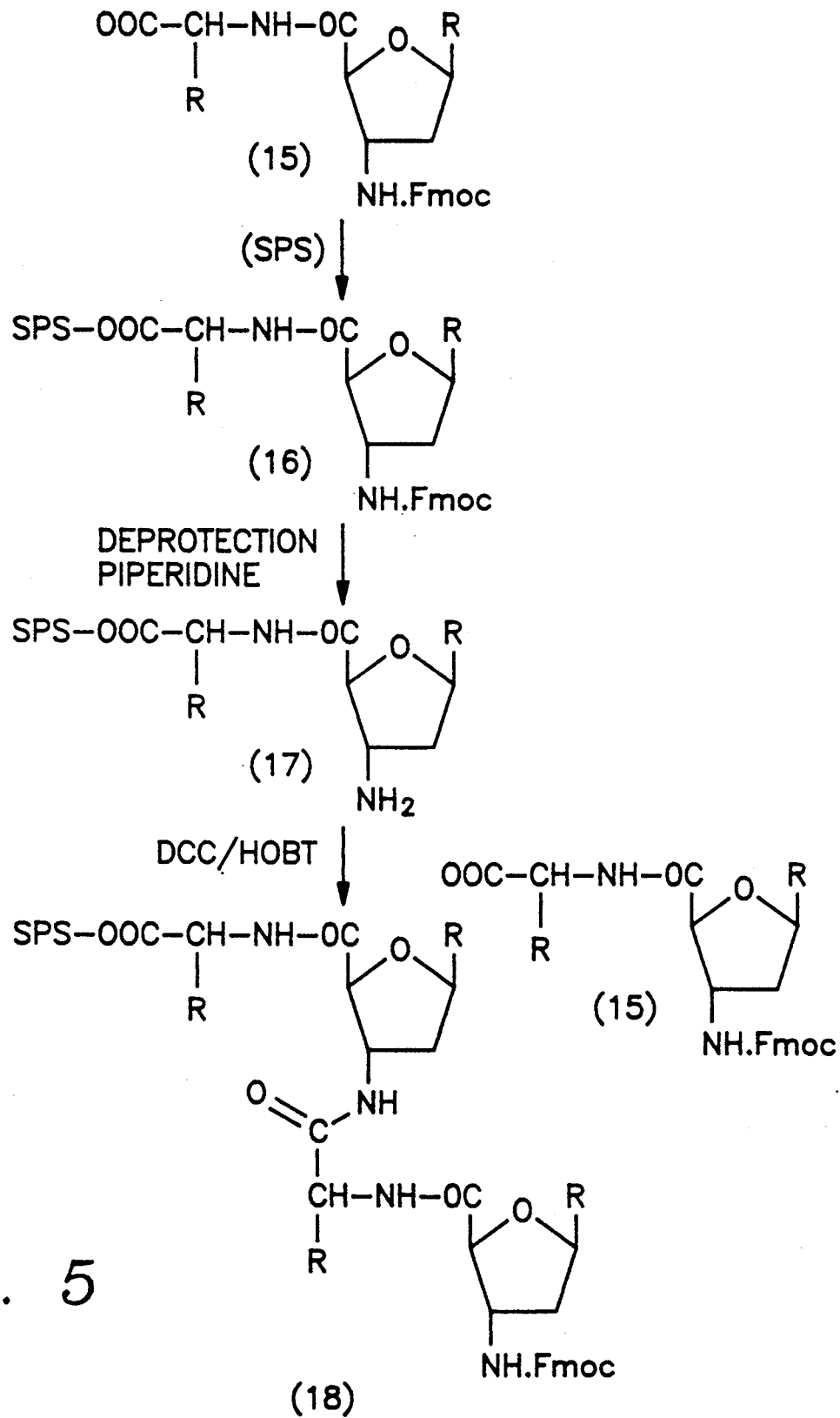
FIG. 5 is an alternate schematic representation of a solid phase synthesis of oligonucleosides with an amino acid backbone.

In the preferred embodiment, the reactions are carried out by solid phase synthesis of the polymeric nucleoside. Each nucleoside contains a nucleo-base, a sugar moiety and an amino acid backbone. In this procedure, the first step is the linkage of compound (I) to a solid phase support, followed by the synthetic procedures described above and shown in FIGS. 2-4 and 6, 7 and 10. A further enhancement is the coupling of the solid phase compound with 9-fluorenylmethyl (Fmoc) amino acid, then deprotecting the amine functionality with piperidine, coupling a monomer nucleoside in the presence of a coupling reagent (for example, dicyclohexylcarbodiimide and 1-hydroxybenzotriazole) and repeating the 9-fluorenylmethyl amino acid coupling, piperidine deprotection and addition of monomer steps until a polymer of sufficient size has been synthesized. The polymer is then removed from the solid phase support (FIGS. 4 and 5).

In another embodiment an oligonucleoside (13) with an amino acid linkage containing sulfur is synthesized. This procedure involves deprotecting compound (14) with piperidine and reacting the deprotected compound with the dithioester (10) (FIG. 4).

Figure 10:
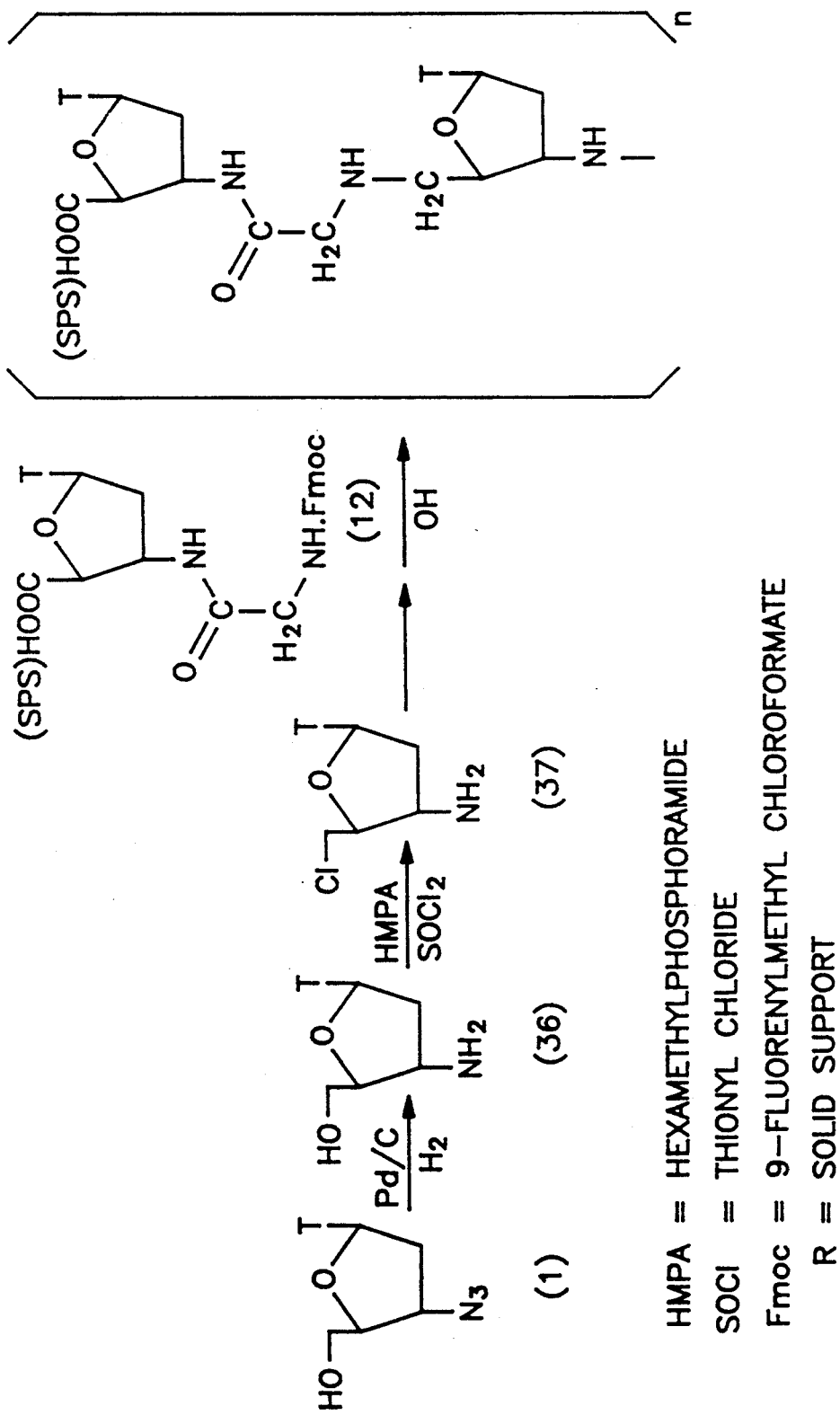
FIG. 10 is a schematic representation of the synthesis of an alternate amide-amine linkage.

A further embodiment is a method for introducing additional flexibility in the internucleoside linkage by replacing one of the amide bonds with an amine (FIG. 10). This method comprises the steps of catalytic reduction of:

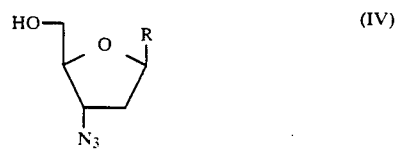
(IV)

wherein R is a nucleo-base; chlorination of the hydroxymethyl function with hexamethylphosphoramidethionyl chloride reagent; and base catalyzed condensation with:

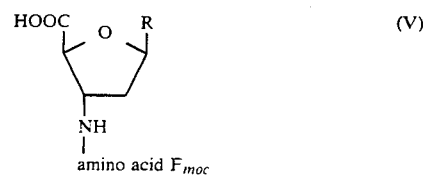
(V)

An additional carbon unit can be introduced into the amino acid linkage by oxidation of 5,-cyano-3'-azido-3',5'-dideoxythymidine (VI) under basic conditions. This general procedure is applicable to other nucleo bases.

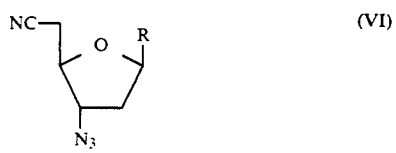
(VI)

The following examples are offered by way of illustration and are not intended to limit the invention in any manner. In examples, all percentages are by weight, if for solids and by volume if for liquids, and all temperature are in degrees Celsius unless otherwise noted.

EXAMPLE 1

Synthesis of the Thymine Derivative of Compound (I)

The present invention is designed to generate amine and carboxylic acid functionalities on the carbohydrate moiety of the nucleoside monomer at 3'- and 4'-positions, respectively. An example of the approach for thymine is seen in FIG. 1. Synthesis of the thymine derivative (2) of (I) was achieved in an efficient manner by the oxidation of commercially available 3'-azido-3'-deoxythymidine (1).

To achieve this oxidation, a high yield method to selectively oxidize the 5'-hydroxymethyl functionality in pyrimidine nucleosides using ruthenium tetroxide was developed. Until the present invention, other oxidative approaches using potassium permanganate, Pt/O₂ or RuCl₃/NaIO₄ have been used. These other approaches have found limited application, however, due to the tendency of these reagents to produce pyrimidine ring opening.

A novel feature of the present invention using ruthenium tetroxide, is its applicability to pyrimidine nucleosides where ring opened side products are generally formed during the traditional oxidation methods. Using the procedure of the present invention, formation of such side products have not been observed after using a variety of 2',3'-isopropylidene purine and pyrimidine nucleosides. Since thymidine is the most sensitive base to such oxidative ring opening, the generality of the present invention was confirmed by using thymidine as the substrate for oxidation activation (FIG. 1).

Oxidation of 1.07 g of Compound (1) catalyzed by ruthenium tetroxide generated in situ by the treatment of 20–25 mg ruthenium trichloride (RuCl$_3$) with 4.40 g potassium persulfate (K$_2$S$_2$O$_8$) in 40 ml of 1M aqueous KOH at ambient temperature gave 0.9 g of crystalline 1-(3-azido-2,3-dideoxy-$\beta$-D-erythro-pentofuranosyl-5-uronic acid)thymine (2). The isolated yield of the analytically pure (2) was 80%.

Characteristics of compound (2):

IR(neat): 3440, 2109(N$_3$), 1744, 1712, 1697 and 1606 cm$^{-1}$;

$^1$H NMR(DMSO-d$_6$): $\delta$ 1.77(s,3H, CH$_3$), 2.05–2.25(m,2H,2-H'&2-H"), [4.13, 4.45, 6.13] (1H each, 4'H,3'H,&1'H) and 9.07(s,1H,C$_6$-H);

$^{13}$C NMR(DMSO-d$_6$): $\delta$172.16(COOH),[163.76, and 150.43](Base —C=O's), 138.43(C$_6$), 106.50(C$_5$), [64.93, 64.45, 65.08, and 36.5](sugar C's) and 12.12 (CH$_3$);

Anal. Calcd for C$_{10}$H$_{11}$N$_5$O$_5$: C,42.71; H,3.94; N,24.91. Found: C,42.63; H,3.76; N,25.24.

EXAMPLE 2

Synthesis of Thymine Amino Acid Nucleoside (5)

Figure 2:
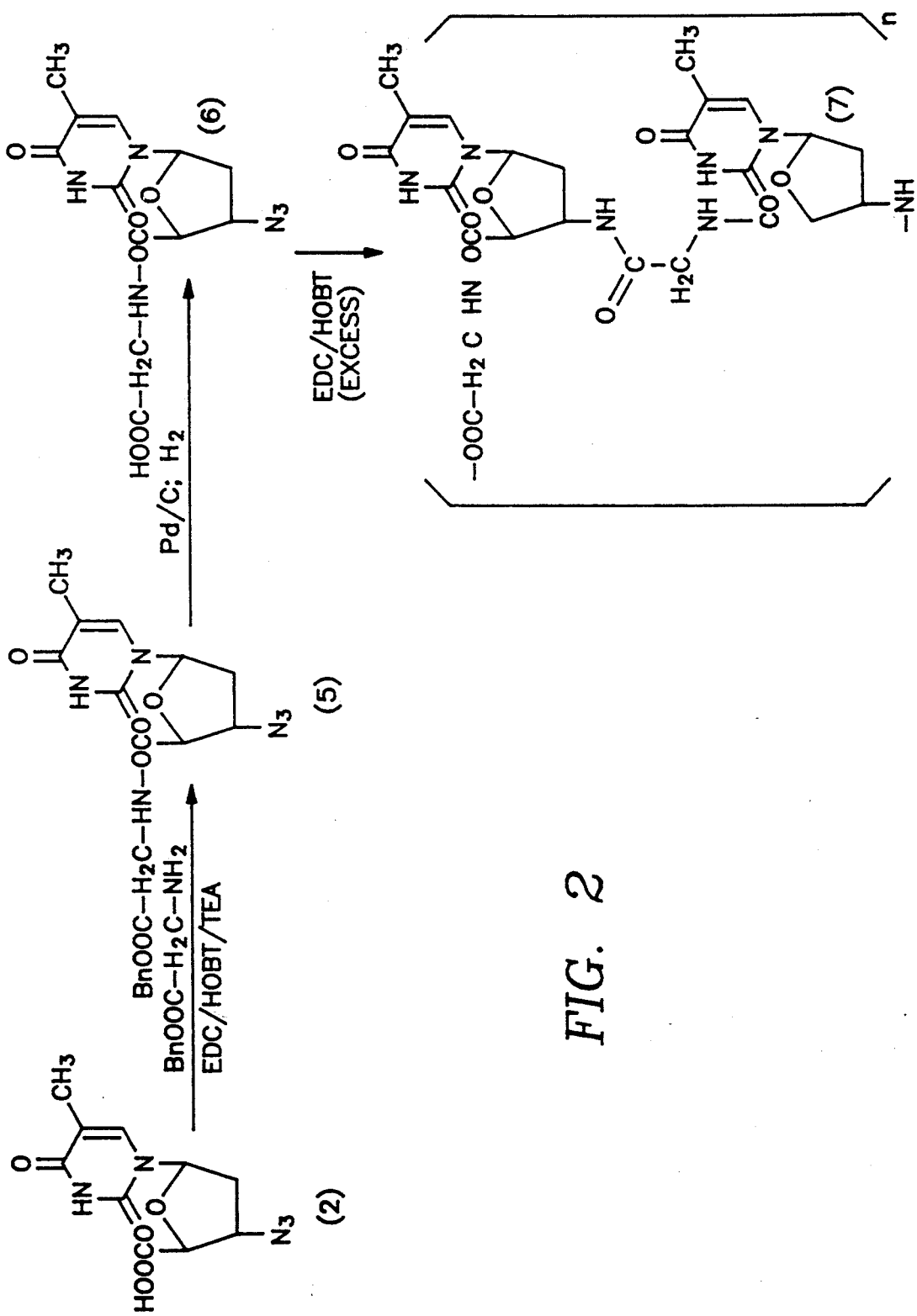
FIG. 2 is a schematic representation of the forming of a nucleoside with amino acid backbone and the formation of an oligonucleoside containing an amino acid backbone.

As seen in FIG. 2, there is the formation of an amide link between the 5' nucleoside carboxylate and a protected amino acid. Compound (15) 0.28 g was coupled with 0.242 g glycine benzyl ester in 20 ml anhydrous dimethylformamide(DMF) using 0.167 g 1-hydroxybenzotriazole(HOBT) and 0.267 g 1-ethyl-3-[3-dimethylamino)propyl]carbodiimidehydrochloride (EDC), in the presence of 0.18 ml triethylamine (TEA) to yield 0.325 g of the 1-3-azido-2,3-dideoxy-$\beta$-D-erythropentofuranosyl-5-glycine benzyl uronate)thymine (5) as colorless plates. The yield was 76%. Characteristics of Compound 5:

IR(neat): 3332, 2109(N$_3$), 1747 and 1696 cm$^{-1}$;

$^1$H NMR(CDCl$_3$): $\delta$ 1.89(s,3H,CH$_3$, 2.2–2.5(m,2H,2'-H), 3.92(m,1H,4'-H), 4.57(m,1H,3'-H), 5.19(2H,—CO—CH$_2$NH), 6.21(dd,1H,1'H) and 7.34(s,5H,C$_6$H$_5$);

$^{13}$C NMR(CDCl$_3$): $\delta$ [169.35, 162.99, 150.24, and 135.07] (—C$_{\odot}$O's), 136.17(C$_6$), [128.57, and 128.28] (Ar-C), 112.35(C$_5$), 87.67(C$_{1'}$), 83.17 (C$_{4'}$), 67.44(C$_{2'}$), 63.51(C$_{3'}$), [41.05, and 35.25](CH$_2$'s) and 12.10(CH$_3$);

Anal. Calcd for C$_{19}$H$_{20}$N$_6$O$_6$: C,53.27; H,4.70; N,19.62. Found: C,53.26; H,4.64; N,19.66.

The catalytic hydrogenation of 0.415 g compound (5) in 40 ml methanol in the presence of 10% Pd/C at 40 psi for 3 h yielded 0.218 g (72%) of the key monomer 1-(3-amino-2, 3-dideoxy-$\beta$-D-erythro-pentofuranosyl-5-glycine uronate)thymine (6). Thus, the thymine nucleoside was synthesized in essentially three high yield steps from (1);

Characteristics of the thymine nucleoside (6):

UVmax(H$_2$O): 190 nm($\epsilon$21000), and 268(10000);

IR(neat):3200-2600(br), 1744, 1712, 1697, and 1666 Cm$^{-1}$;

$^1$H NMR(DMSO-d$_6$): $\delta$ 1.78(s,3H,CH$_3$), 2.10–2.15(m,2H,2'H-2"H), 3.70 (br,2H,NH$_2$), 6.33(dd,1H,1'H) and 8.05(s,1H,C$_6$H);

$^{13}$C NMR (DMSO-d$_6$): $\delta$[170.72 and 170.13] (COOH - COHN), [163.38 and 150.25] (base —C=O's), 136.31(C$_6$), 109.21(C$_5$), [64.64, 64.11, 54.67, 41.27, and 37.61] (sugar C's and CH$_2$'s) and 11.60(CH$_3$).

Reaction of the amino acid nucleoside in excess DCC/HOBT produced the oligonucleotide (7). Although synthesis of the thymidine derivative is shown in FIG. 2, one skilled in the art readily recognizes that by substitution of the appropriate base (A,T,G,C,X,and I) an oligonucleotide of a specific sequence can be synthesized.

EXAMPLE 3

Esterification

Figure 3:
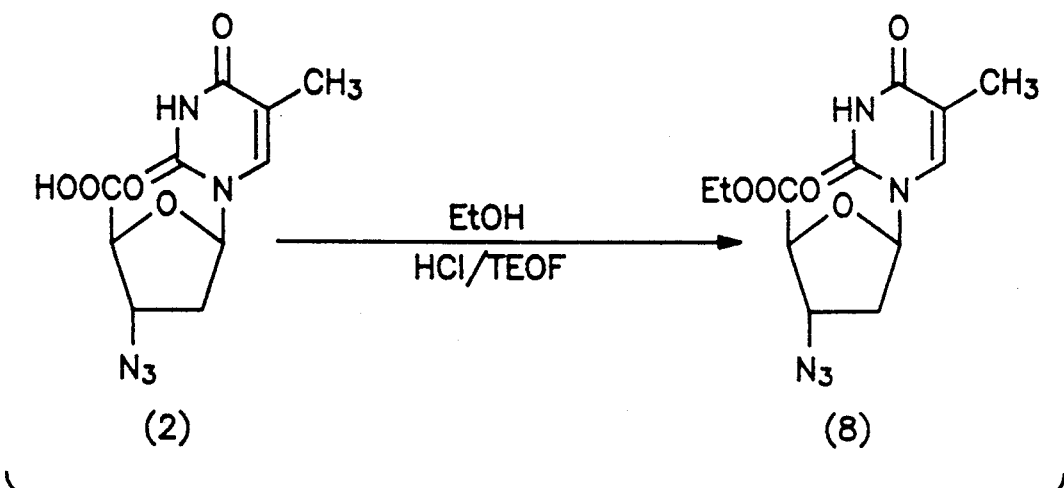
FIG. 3 is a schematic representation of the formation of the ester of the compound (I), wherein R' is ethyl.

The esterification of 0.18 g of compound (2) with 10 ml of anhydrous EtOH saturated with HCl in triethyl orthoformate (TEOF) yields 0.15 g (75%) ethyl- 1-(3-azido-2,3-dideoxy-$\beta$-D-erythro-pentofuranosyl-5uronate)thymine (8) (see FIG. 3).

Alternatively, Compound (8) was obtained from 10 g of Compound (2) via esterification with 20 ml of ethanol in the presence of DCC/DMAP. This is a valuable precursor with a blocked carboxylic acid end for further elaboration at the 3'-amino functionality. Characteristics of Compound (21):

$^1$H NMR(DMSO-d$_6$): $\delta$ 1.36(t,3H,CH$_3$), 1.96(s,3H,5-CH$_3$), 2.15–2.55(m,2H,2'-H), 4.19–4.56(m,4H,C-H$_2$—CH$_3$,3'-H,4'-H), 6.38(dd,J=5.4Hz,1H,1'-H) and 7.94(s,1H,H-6).

EXAMPLE 4

Synthesis of 3'-amino-3',5'-dideoxy thymidine 5'-Carboxylic Acid (9)

Synthesis of (9) is shown in FIG. 4. The catalytic hydrogenation of 1 g of compound (2) in 100 ml methanol in the presence of 10% Pd/C at 45 psi for thirty minutes yielded 0.35 g of crystalline 1-(3-amino-2,3-dideoxy-$\beta$-D-erythro-pentofuranosyl- 5-uronic acid) thymine (9) as colorless platelets;

Characteristics of Compound (22):

$^1$H NMR(DMSO-d$_6$): $\delta$ 1.75(s,3H,CH$_3$), 2.0–2.45(m,2H,2'-H), 3.90 (m,1H,4'—H), 4.25(m,1H,3'—H), 5.34(br,NH$_2$), 6.35 (d,J=6.6Hz,1H,1'—H) and 8.8(s,1H,C$_6$—H);

Anal. Calcd for C$_{10}$H$_{13}$N$_3$O$_5$.¼ H$_2$O : C,46.24; H,5.23; N,16.18. Found: C,46.08; H,5.29; N,16.00.

EXAMPLE 5

Formation of a 3' Amide Link Between the Amine and a Blocked Amino Acid

Alternative synthetic routes were developed to conjugate the amino acid linker to the 3'-, rather than the 5'-end of the nucleoside. An example of this synthetic route is seen in FIG. 4.

Treatment of 2.5 g of Compound (9) with 3.1 g of 9-fluorenylmethyl choloroformate (Fmoc chloride) in the presence of N,N,-diisopropylamine (1.5 g) in dry DMF (25 ml) at room temperature for an hour gave the corresponding Fmoc derivative (11) in a 74% yield. This derivative can be manipulated at the 4'-carboxylate end and converted to dithioester (10) using 2,4-bis(ethylthio)-2,4-dithioxocyclo-di-$\lambda^5$-phosphathiane. Compound (10) will prove useful in the preparation of oligonucleosides with amino acid linkages containing sulfur, as exemplified in Compound (13) (with glycinate) (FIG. 4).

FIG. 4 shows the coupling of (9) with Fmoc-glycine in the presence of EDC/HOBT yields 1-(3-glycineamido-2,3-dideoxy-β-D-erythro-pentofuranosyl-5-uronic acid) thymine (12). Employing a similar coupling procedure, after deprotection of compound (12) with piperidine and subsequent reaction with compound (11) yields the dimer (14). Thus, by repetitive deprotection with piperidine and reaction in DCC/HOBT with a $F_{moc}$ derivative of the nucleoside an oligonucleoside of desired length can be synthesized. Although only the thymidine derivative is shown in this example, one skilled in the art readily recognizes that by substituting the various nucleosides (A,T,G,C,X,I) an oligonucleotide with a specific sequence can be synthesized.

Alternatively, the target oligonucleoside with amino acid backbone can be synthesized using nucleoside-amino acid conjugate by a standard solid phase methodology (FIG. 5).

The protection of amino group of (6) by the conventional procedure (Fmoc protection) yields (15), which on subsequent deprotection (piperidine) will provide free amino compound (17). Further condensation of (17) with (15) in the presence of DCC/HOBT in dimethylformamide will yield (18) (FIG. 5).

EXAMPLE 6

Large Scale Preparation of 3'-Azido Nucleosides

1. Thymidine derivative. The 3'-azido nucleosides are synthesized in large scale for use in the amide coupling procedure. For example (1) is synthesized as described in FIG. 1, in high yield by employing a known procedure via the intermediate 2,3'-anhydrothymidine (3). For example, compound (3) is prepared using relatively inexpensive thymidine and diphenyl sulfite. Rao & Reese, J. Chem. Soc., Chem. Comm. 997 (1989). The ruthenium tetraoxide oxidation as described earlier, yields the corresponding acid (4). Upon warming the acid (4) with 2 molar equivalents of lithium azide in dimethylacetamide solution yields (2) in gram quantities. Thus from 5 g of the 2,3'-anhydrothymidine derivative (3), 3.5 g of (2) was synthesized. This provides an efficient and relatively inexpensive method for monomer synthesis.

2. Cytidine, adenosine and guanosine derivatives:

The synthesis of the amino acid-nucleoside monomers containing 2'-deoxycytidine, 2'-deoxyadenosine and 2'-deoxyguanosine are prepared from the corresponding 3'-azido derivatives by oxidizing the 5'-hydroxymethylene functionality. The starting material 3'-azido-2',3'-dideoxycytidine (19a) or 3'-azido-2',3'-dideoxyadenosine (19b) were synthesized in gram quantities employing known methods, for example see, Lin and coworkers, J. Med. Chem. 26:1691 (1983). The corresponding guanosine analog, 3'-azido-2',3'-dideoxyguanosine (28) is prepared by the known transglycosylation procedure. Imazawa and Eckstein, J. Org. Chem. 93:2102 (1978). The protection of the exocyclic amino groups of the bases follows standard protocols (see FIGS. 6 and 7).

3. Oxidation of the 3'-Azido-2', 3'-dideoxynucleosides

The ruthenium catalyzed oxidation procedure as described above for the thymidine is followed for all nucleosides. The 3'-azidonucleoside (1 mM) (19a, 19b or 28) in 1M potassium hydroxide solution (10mL) is treated with potassium persulfate (3–4 mM) in presence of 2–5 mg of ruthenium trichloride trihydrate with constant stirring for 3 h. The reaction is monitored by silica gel TLC: (BuOH:AcOH:H$_2$O; 5:3:2, v/v). Upon completion, the pH of the reaction mixture is adjusted to 7–8 with dilute HCl, solvent removed and the product (20a, 20b or 29) purified by column chromatography on silica gel (see FIGS. 6 and 7).

EXAMPLE 7

Polymer Synthesis

The polymerization of the T'gly monomer (6) was accomplished using the standard DDC coupling reaction in the presence of HOBT. A 10 fold excess of the DDC and HOBT are employed in anhydrous DMF with monomer concentration of 10 mg/ml. Removal of the solvent and addition of methanol precipitated the polymer. The precipitated polymer dissolved readily in water at a solubility limit near to 1 mg/ml at pH 7, room temperature (approximately 5 mgs/ml at pH 9.5).

EXAMPLE 8

Polymer Fractionation and Preliminary Characterization

The resulting distribution from polymer synthesis can be fractionated employing NACS ion-exchange HPLC, and using an ammonium acetate gradient. The size of the resulting (T'gly)$_n$ oligomers was estimated by quantitative labeling of the amino terminus with malachite green isothiocyanate, then comparison of the absorbance of the resulting conjugates at 270 nm vs 620 nm. Based upon this analysis, the above described polymerization reaction results in an average chain length of 20 bases.

EXAMPLE 9

Thermal Stability Analysis

To demonstrate that the resulting T'gly polymers are capable of duplex formation with a standard phosphodiester complement, a mixing analysis was performed. Increasing concentration of (T'gly)$_n$ was added to high molecular weight polydA. The resulting change of UV absorbance properties was monitored. The T'gly polymer was fractionated by pressure filtration on a centricon membrane with 10,000 MW cutoff to yield a heterogeneous polymer population with length greater than about 30 bases.

Figure 8:
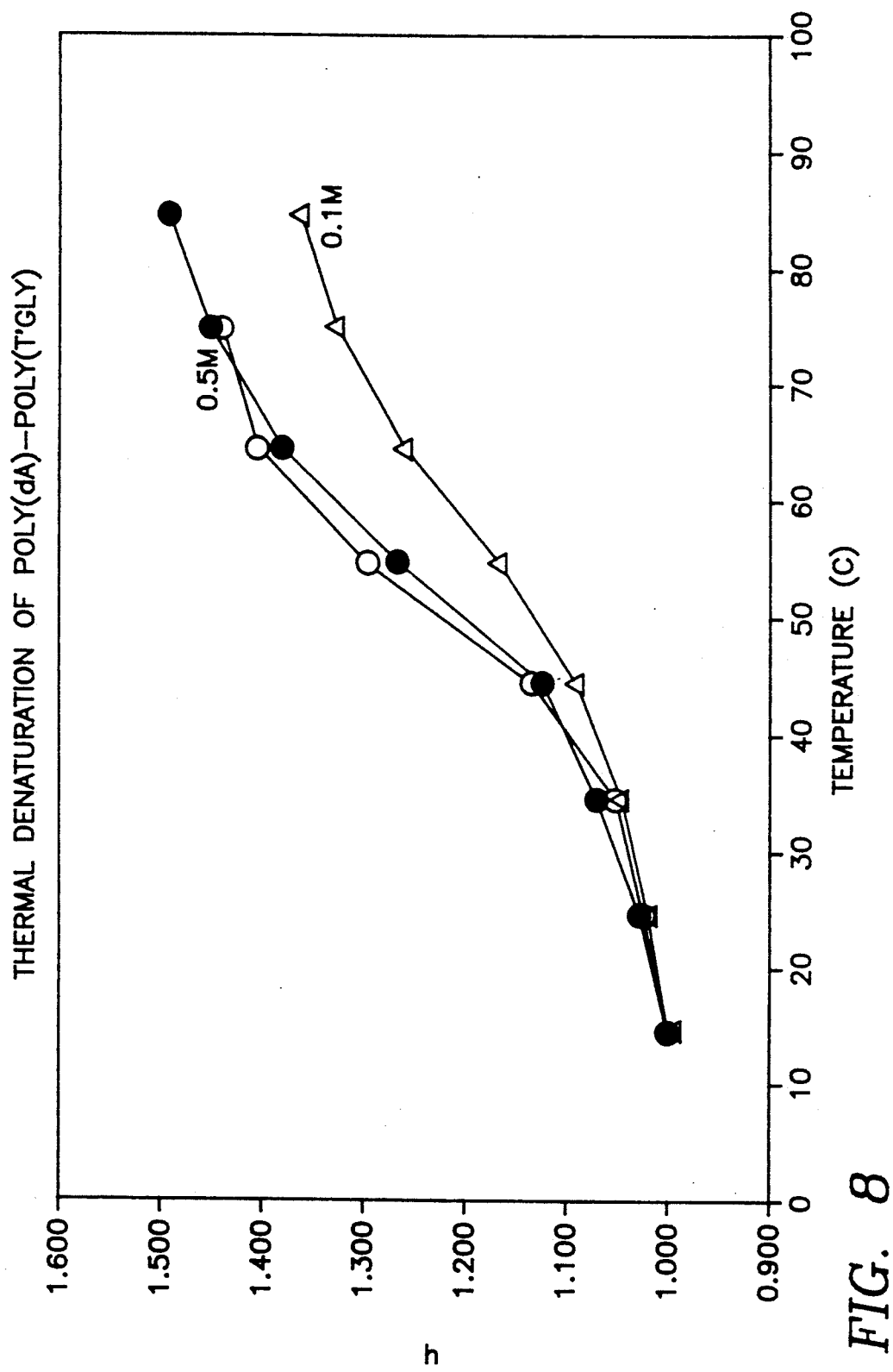
FIG. 8 is a graph showing the thermal denaturization of poly(dA)-poly(T'GLY) as a function of temperature.
Figure 9:
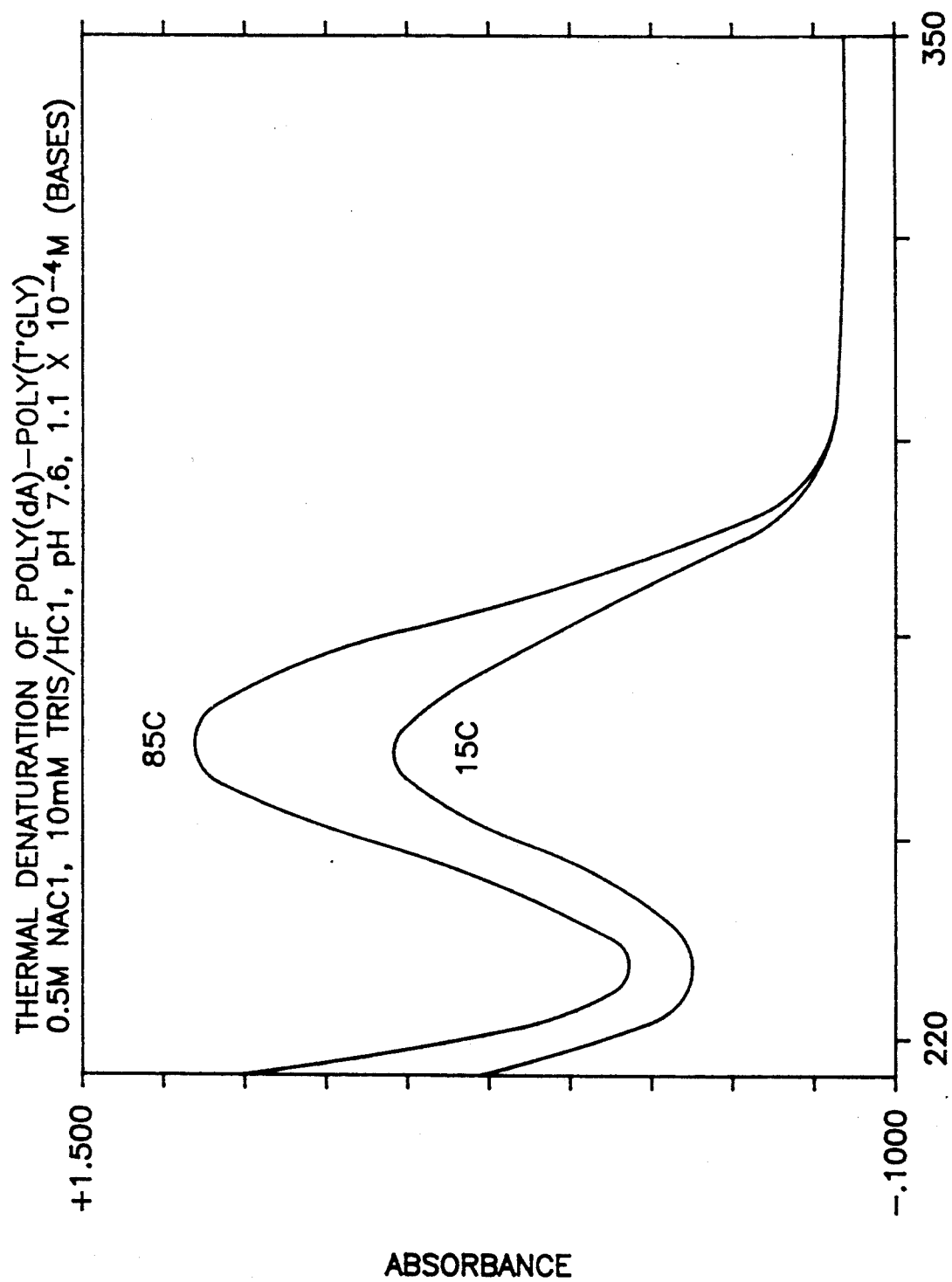
FIG. 9 is a graph showing the thermal denaturization of the poly(dA)-poly(T'GLY) of absorbance at temperatures of 10° C. and 85° C.

As seen in FIGS. 8 and 9, a 1/1 polydA-(T'gly)$_{30}$ complex displays 50% thermal hyperchromism, with an apparent Tm of 55°, in 0.5M NaCl, 10 mM Tris/HCl pH 7.6, $1.1 \times 10^{-4}$M in total base equivalents. When the counterion concentration is reduced to 0.1M, the apparent Tm for the 1/1 complex is increased by approximately 10° to 65° C. The observed hyperchromism is as expected for an orderly duplex and the average Tm for the population is comparable for high molecular weight polydA-polydT under similar conditions of ionic strength.

EXAMPLE 10

Chemical Stability

To assess the chemical stability of the amide linkages in the synthesized compounds, the monomer (6) (T'gly) was subjected to hydrolysis in 30% NH$_4$OH at 55° C. for 24 h. As assessed by TLC, no hydrolysis of the amide linkage was detected during this treatment. Thus, the amide bond appears to be stable with respect to general base catalyzed hydrolysis. From a practical perspective, this stability to 30% NH4OH at 55° C. confirms that the amide linkage can withstand the hydrolysis required to remove base protecting groups which are necessary for polymerization of A,C and G homologues.

EXAMPLE 11

Synthesis of an Alternative Amine-Amide Linkage

More flexibility can be introduced into the internucleoside linkage by replacing one of the amide bonds with an amine linkage. Compound (1), is reduced in the presence of 10% Pd/C,H$_2$ to yield the required 3'-amino-3'-deoxythymidine (36). Chlorination of (36) with hexamethylphosphoramide-thionyl chloride reagent provides 3'-amino-5'-chloro-3',5'-dideoxythymidine (37). The base catalyzed condensation of (37) with (12) yields (38) (see FIG. 10).

EXAMPLE 2

Coupling to yield nucleoside-amino acid monomers: glycine, serine, phosphoserine, lysine and arginine The power of the invention described herein is that the physical properties of the oligonucleoside-amino acid co-polymer can be altered by amino acid substitution, while keeping the basic synthetic chemistry the same.

Figure 11:
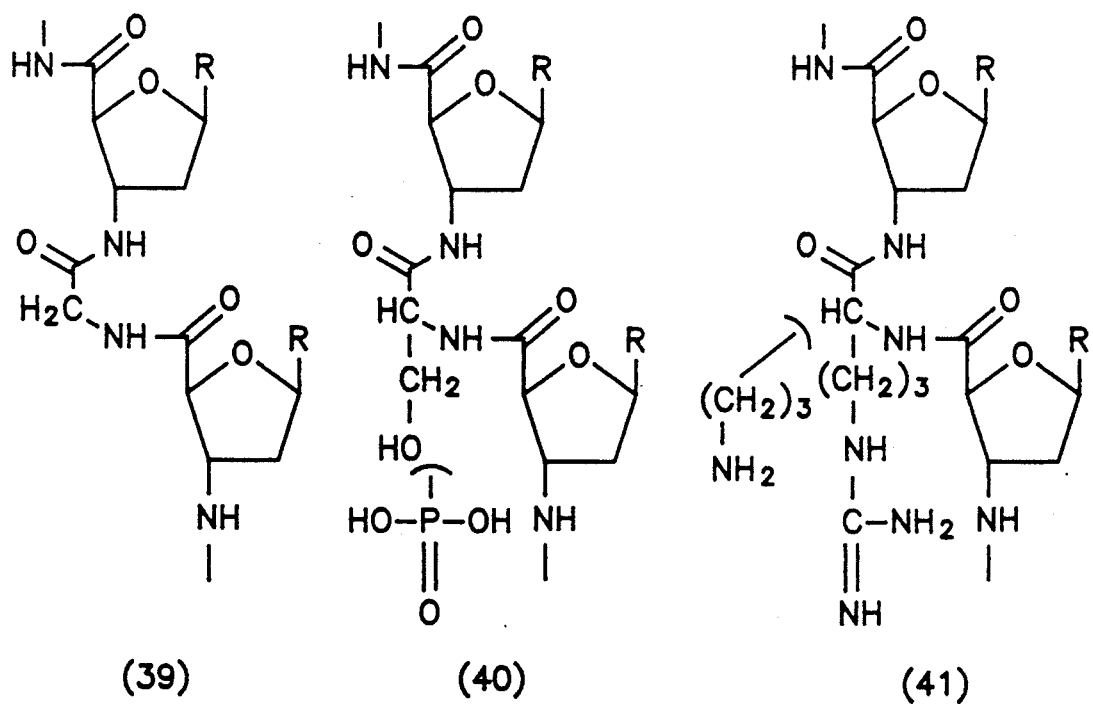
FIG. 11 is a representation of different oligonucleosides with an amino acid backbone, e.g. the glycine linkage (39), serine or phosphoserine linkage (40) and arginine or lysine linkage (41).

1. Serine and Phosphoserine. Serine linked homopolymers (40) (FIG. 11) are synthesized as described for the corresponding glycinates, by condensation with the corresponding serine benzyl ester. The phosphoserine (40) linked oligonucleosides are prepared from the corresponding serine linked oligomers by direct post-synthetic phosphorylation with POCl$_3$ in trimethyl phosphate or in aqueous pyridine. The extent of phosphate modification is confirmed by elemental analysis and $^{31}$P NMR.

2. Lysine. The lysine linked oligomers, (41) (FIG. 11) is synthesized from the ϵ-acetyl lysine benzyl ester which is commonly used for standard Fmoc polypeptide synthesis. The acetyl blocking group is removable in 9M NH4OH (concomitant with base deblocking) and remains stable during the carbodiimide coupling steps required for the solution phase homopolymer synthesis. For iterative solid phase methods the more stable ϵ-benzoyl amine modification may be required. Such protection is reminiscent of the procedure used for the base amines and can be removed by hydrolysis in ammonia.

3. Arginine. The arginine linked oligomers, (41) (FIG. 11) is synthesized from the corresponding arginine benzyl ester. Because of the pK$_a$ difference, guanidinium blocking is not required for the synthesis of homopolymers. For solid phase methods, however, the guanidinium group is protected with a nitro group. This nitro group is removable after polymerization by catalytic hydrogenation.

4. Glycine. The glycine linked oligomers (39) (FIG. 11) were synthesized starting from the glycine benzyl ester. Example of their synthesis is shown in FIGS. 2, 4, 6 and 10.

EXAMPLE 13

Coupling of 3'-Azidonucleoside-4'-Carboxylic Acids with Benzyl Esters of Amino Acids A mixture of 3'-azido-2',3'-dideoxynucleoside-4'-carboxylic acid (1 mM), benzyl ester of amino acid (1.2 mM) and 1-hydroxybenzotriazole monohydrate (HOBT, 1.24 mM) in anhydrous DMF is cooled in ice and treated with 1-ethyl-3-[3-(dimethylamino)propyl]-carbodiimide hydrochloride (EDC, 1.4 mM) and triethylamine (TEA, 1.26 mM). The reaction is stirred at 0° C. for 3 h. then at room temperature overnight. After removal of the solvent, the crude product is purified on a silica gel column followed by crystallization from methanol.

The concomitant removal of the benzyl protecting group and the reduction of 3'-azido moiety is achieved by catalytic hydrogenation using 10% Pd/C in methanol at 40 psi for 3 h. This procedure reproducibly yields a single product after filtration of the catalyst and precipitation with anhydrous ether. Further purification to analytical standards is achieved by preparative isocratic C$_8$ HPLC in 95% H$_2$O/5% methanol. A further advantage of these milder deprotecting conditions is that virtually no racemization of the amino acid backbone occurs.

EXAMPLE 14

Modification of the General Coupling Scheme to the Four Standard Nucleosides

Thymidine was prepared as described above (FIG. 2, compound 5). The corresponding benzyl esters of serine, ϵ-acetyl lysine and arginine are prepared and coupled by the same procedure.

Figure 6A:
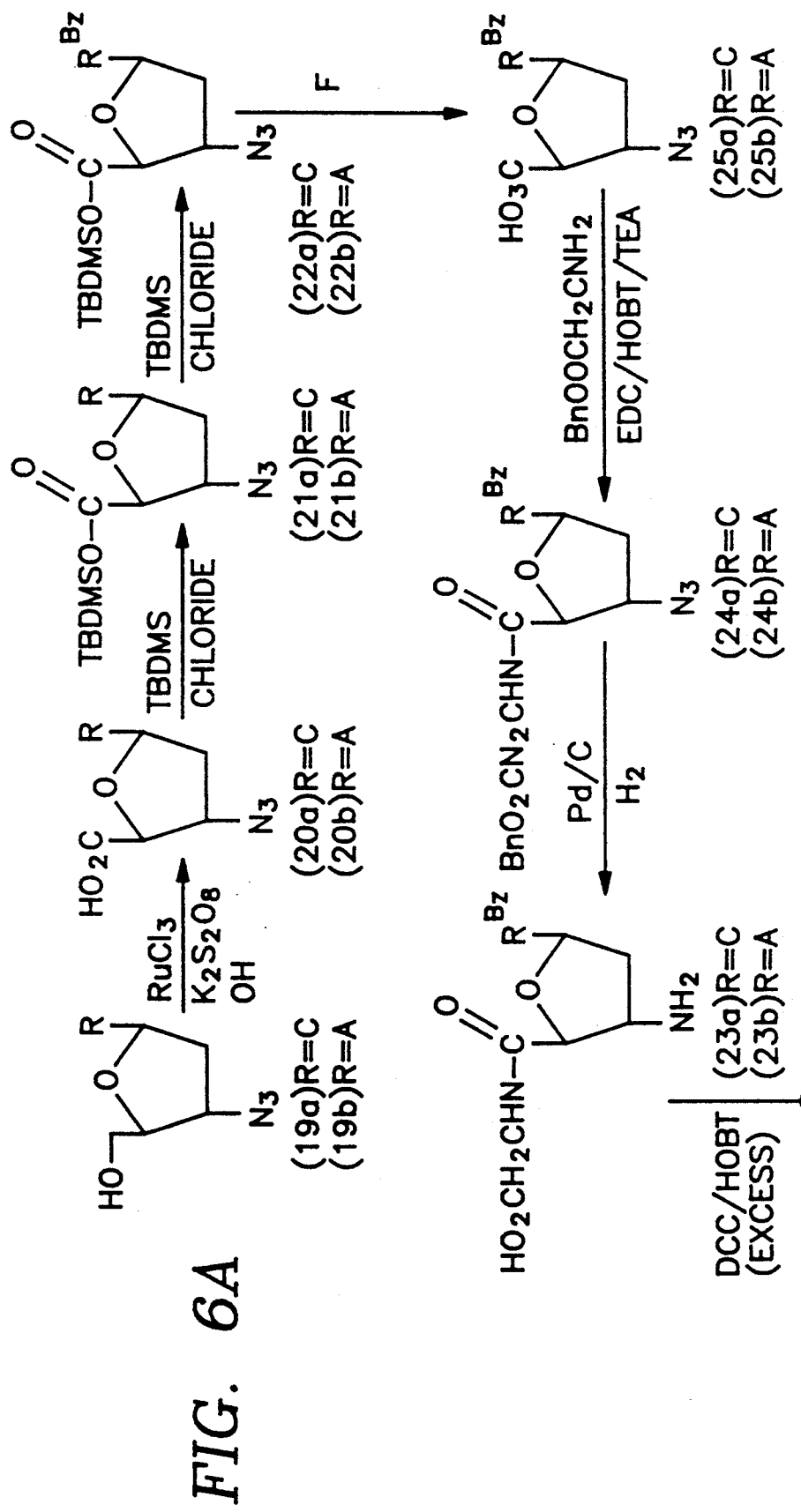
FIGS. 6A and 6B are schematic representation of the synthesis of cytidine or adenosine glycine conjugates, monomers and the oligomers.
Figure 6B:
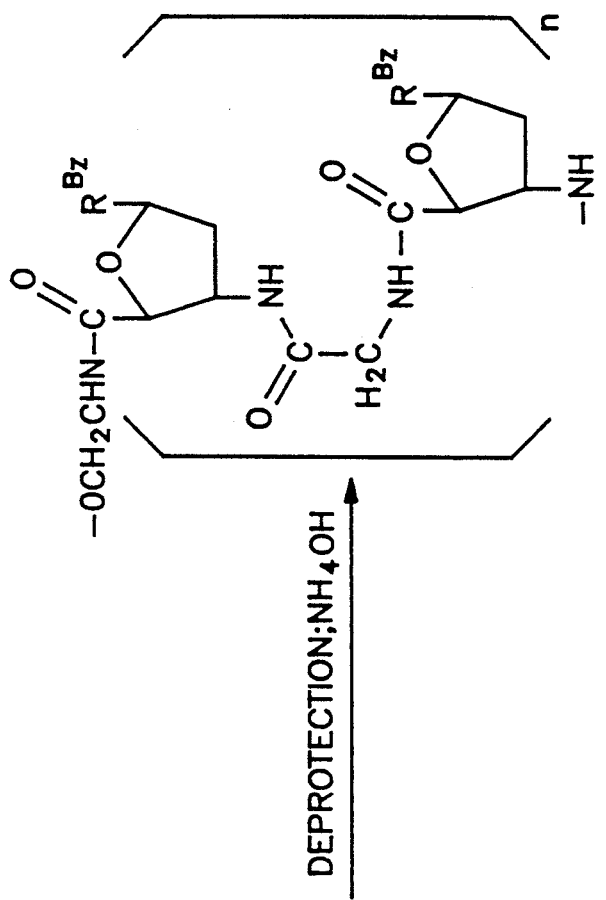
Figure 6B:
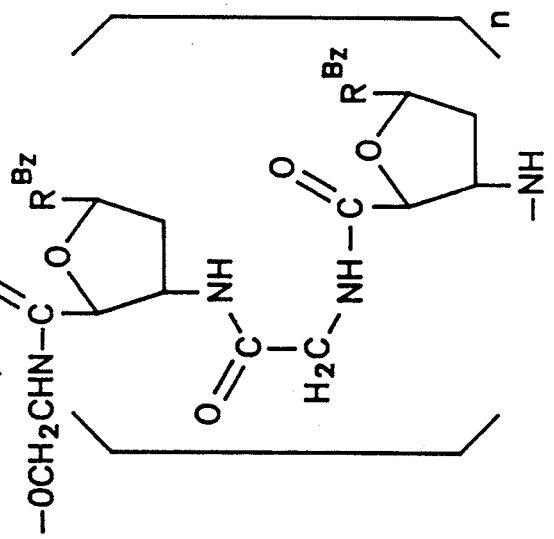
Figure 7A:
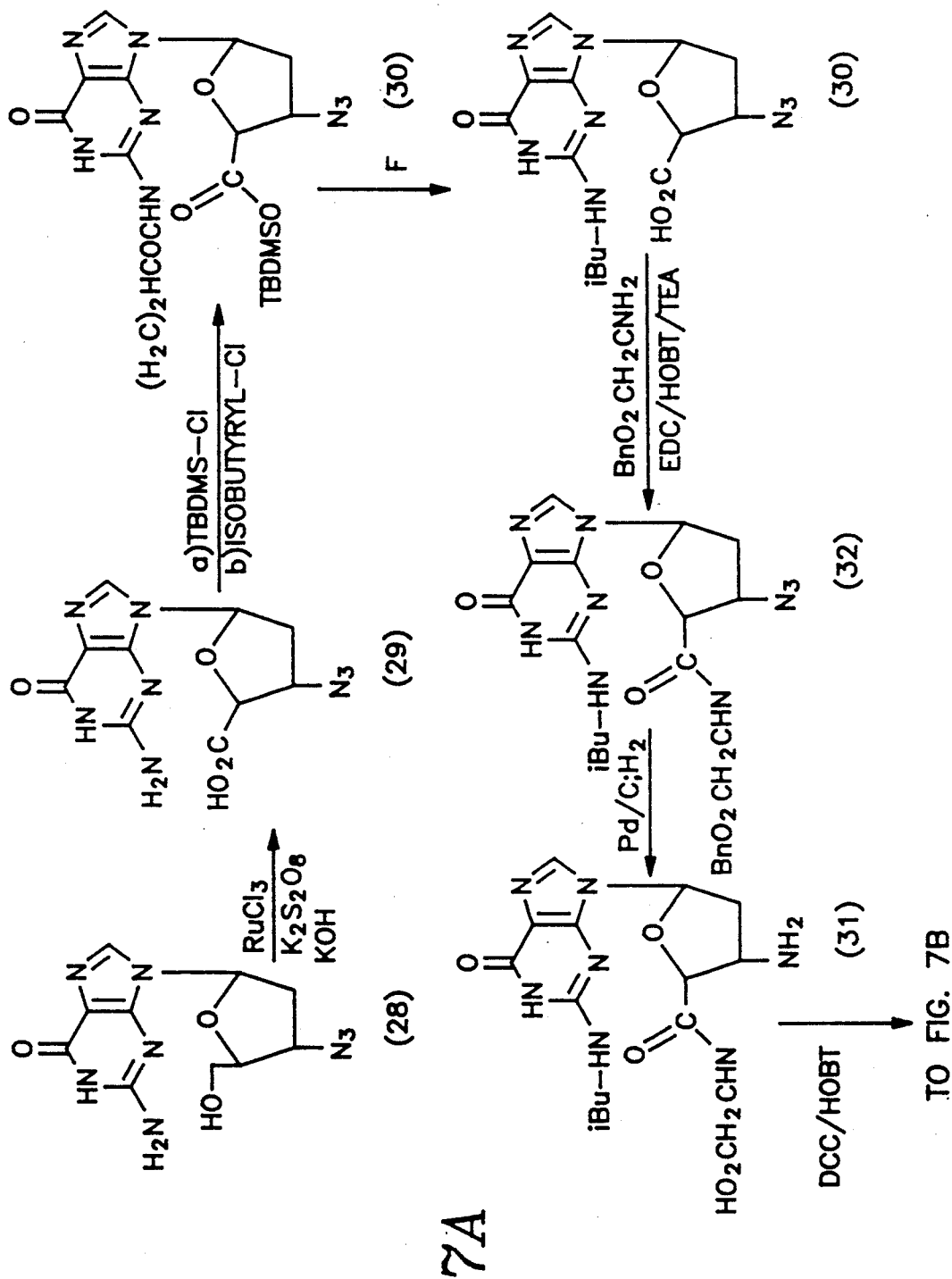
FIGS. 7A and 7B are schematic representations of the synthesis of guanosine glycine conjugate monomer and oligomers.
Figure 7B:
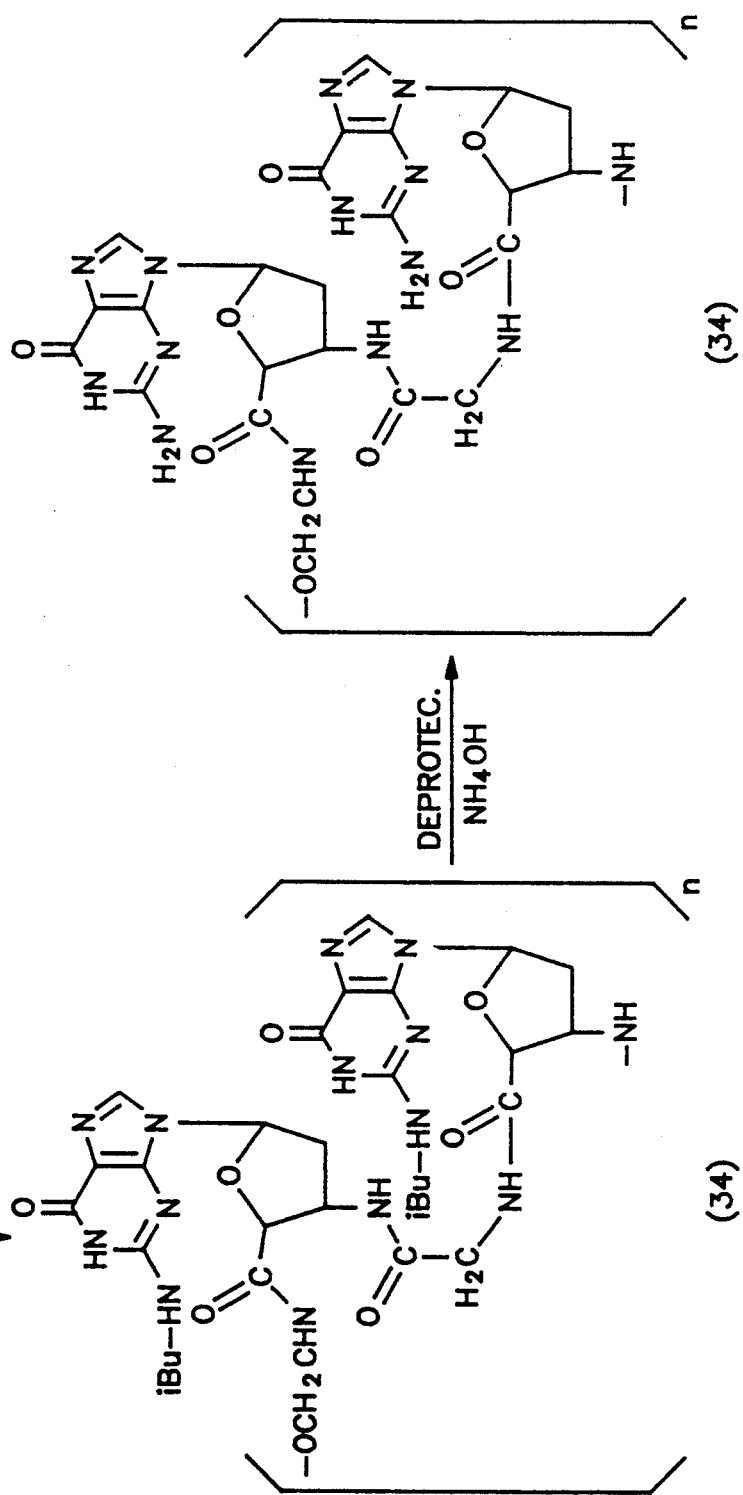

2. Cytidine. The already synthesized azido compound, 3'-azido-2',3'-dideoxycytidine (19a) is oxidized with ruthenium tetraoxide as described for (1) to give the corresponding carboxylic acid (20a). (see FIG. 6). The carboxylic and amino functions of (20a) are protected by the treatment with t-butyldimethylsilyl chloride (TBDMS-Chloride) and benzoyl chloride respectively, to yield (22a). Selective deprotection of the carboxylic group of (22a) is achieved by fluoride ion (tetrabutylammonium fluoride) to yield 1-(3-azido-2,3-dideoxy-β-D-erythro-pentofuranosyl-5-uronic acid)-N$^4$-benzoyloytosine (25a). Condensation of (25a) with glycine benzyl ester in the presence of EDC/HOBT in DMF yields (24a). Upon subsequent hydrogenation, the desired monomer 1-(3-amino-2,3-dideoxy-β-D-erythro-pentofuranosyl-5-glycine uronate)-N$^4$-benzoylcytosine (23a) is produced. This compound (23a) can be polymerized by the carbodiimide chemistry as shown in FIG. 6.

3. Adenosine. Methodology essentially similar to cytidine synthesis is followed to prepare the 2'-deoxyadenosine derivative (23b). The procedure starts from 3'-azido-2',3'-dideoxyadenosine (19b). The 5'-glycinate derivative (23b) is eventually polymerized as described in FIG. 6.

4. Guanosine. The synthesis of the N$^2$-protected 2'-deoxyguanosine building block (30) also follows a similar reaction sequence (see FIG. 7). Oxidation of (28) with ruthenium tetraoxide under alkaline conditions yields 1-(3-azido-2,3-deoxy-β-D-erythro-pentofuranosyl-5-uronic acid)guanine (29). Sequential protection of the carboxylic and amino functionalities of (29) with TBDMS-chloride and isobutyryl chloride, respectively yields 1(3-azido-2,3-dideoxy-β-D-erythro-pentofuranosyl-5-uronic acid)-N²-isobutyrylguanine (30). Coupling of (30) with glycine benzyl ester in the presence of EDC/HOBT in DMF medium yields (32). Upon subsequent catalytic hydrogenation, the desired monomer, 1-(3-amino-2,3-dideoxy-β-D-erythro-pentofuranosyl-5-glycineuronate)-N²-isobutyrylguanine (31) is produced. Polymerization of (31) under standard reaction conditions as described for (6), (23a) and (23b) can provide (34). After deprotection, the homopolymer (35) is produced. The polymer can be purified by HPLC.

EXAMPLE 15

Extension to a Solid Phase Method

The solution state polymerization procedures described above can be readily adapted to solid phase chemistry, by employing the corresponding 3'-Fmoc derivatives of the nucleoside-amino acid monomers (FIGS. 4 and 5). The usual cycle of Fmoc removal and carbodiimide coupling, which is standard for peptide synthesis, is employed for the polymers. Since the amide linkage in the monomer is stable to extended hydrolysis in $NH_4OH$, the cleavage from the solid support and the deblocking is performed simultaneously in 30% $NH_4OH$, 55° C., 24 h.

EXAMPLE 16

Characterization of the Resulting Polymers

One skilled in the art will readily recognize that there are a variety of methods which can be used to characterize the monomers and polymers synthesized in the present invention. Examples of the methods used herein include: chromatography, mass spectrometry and electrophoresis. In chromatography, preparative molecular sieve chromatography (G50) generates polymers of sufficient homogeneity for optical and thermal melting analysis. High resolution fractionation of T'gly polymers is analyzed by NACS anion exchange resin employing ammonium acetate at pH 10.5 as the eluant. In the mass spectrometry analysis, electron spray mass spectroscopy is used. Further, the average chain length of (T'gly)$_n$ oligomers can be estimated by end group determination. Size is also assayed by analytical molecular sieve chromatography. The co-polymers are similar to polypeptides in terms of water solubility and chain dynamics. Thus, for chain lengths greater than 20, the co-polymers can be analyzed by SDS polyacrylamide electrophoresis, visualizing with silver stain or by radiochemical end labelling with a primary amine specific reagent. For polymers with charged backbones or for those with T or G above pH 10, polyacrylamide electrophoresis can also be performed without SDS.

EXAMPLE 17

Duplex and Triplex Binding Analysis

The selectivity and thermodynamic stability of duplexes and triplexes containing nucleo-base-amino acid copolymers are assessed by a band shift method, by UV detected melting and by footprinting methods.

1. Band Shift. The electrophoretic mobility of single strands, duplex and triplexes in the 10–50 base region are distinctly different. This fact has been exploited to monitor the strands to duplex and duplex to triplex binding titrations. One skilled in the art recognize that such a titration is used to estimate the stoichiometry and apparent Kd for the transition. The sequences of the first 27 base long strands to be used for band shift analysis are described below. Notice that they can be employed for both duplex and triplex analysis and that a pair has been introduced to assess the energy cost due to a mismatch.

TABLE 1

| Constructs for binding analysis. | |
|---|---|
| Sites for A'-aa and T'-aa homologues | |
| 5'-AAAAAAAAAAAAAAAAAAAAAAAAAAA-3'<br>3'-TTTTTTTTTTTTTTTTTTTTTTTTTTT-5' | SITES FOR BAND SHIFT |
| 5'-AAAAAAAAAAG̲AAAAAAAAAAAAAAAA-3'<br>3'-TTTTTTTTTTC̲TTTTTTTTTTTTTTTT-5' | |
| 5'-GGGGCCCAAAAAAAAAAAAAAAAAAAAAAAAAAAGGGCTT-3'<br>3'-CCGGGTTTTTTTTTTTTTTTTTTTTTTTTTTTCCCGGGAA-5' | SITES FOR FOOTPRINTING |
| 5'-GGGGCCCAAAAAAAAAAG̲AAAAAAAAAAAAAAAAGGGCTT-3'<br>3'-CCGGGTTTTTTTTTTC̲TTTTTTTTTTTTTTTTCCCGGGAA-5' | |
| Sites for G'-aa and C'-aa homologues | |
| 5'-GGGGGGGGGGGGGGGGGGGGGGGGGGG-3'<br>3'-CCCCCCCCCCCCCCCCCCCCCCCCCCC-5' | SITES FOR BAND SHIFT |
| 5'-GGGGGGGGGGGA̲GGGGGGGGGGGGGGGG-3'<br>3'-CCCCCCCCCCCT̲CCCCCCCCCCCCCCCC-5' | |
| 5'-AAAATTTGGGGGGGGGGGGGGGGGGGGGGGGGGGAAATCC-3'<br>3'-TTAAACCCCCCCCCCCCCCCCCCCCCCCCCCCTTTAAAGG-5' | SITES FOR FOOTPRINTING |
| 5'-AAAATTTGGGGGGGGGGGA̲GGGGGGGGGGGGGGGGAAATCC-3'<br>3'-TTAAACCCCCCCCCCCT̲CCCCCCCCCCCCCCCCTTTAAAGG-5' | |

2. UV and CD detected melting. The thermodynamics of the duplex to strands and triplex to duplex + strand equilibrium is assessed by observing the characteristic absorbance or ellipticity change attendant to the melting transition. Interpretation of such data is well understood in the art to assess thermodynamic parameters (Tm and apparent V.H. enthalpy) of duplex and triplex formation with discrete oligomers, including those with modified phosphodiester backbones.

3. UV and CD analysis. There is a large, well characterized absorbance decrease and induced CD effect associated with duplex or triplex formation. As seen in its UV absorbance band (FIG. 9), the nucleo base-amino acid copolymers differ from standard oligomers in that they possess a chromophore in both the nucleoside and in the linker. The optical properties of both moieties are examined to compare the gross structure of the corresponding duplexes and triple helices.

4. Footprinting. Because they possess an amino terminus at their 3' end, the nucleo base-amino acid copolymers were modified at the N terminus with photochemicals or with DTPA to generate a site for iron chelation and subsequent Fenton chemistry. These two methods were used to confirm the preferred strand orientation in duplexes and triplexes. Eosin can be used as the photochemical, because it binds weakly to DNA on its own. The activated amine modifier DTPA was chosen as a selective chelator for the Fenton reaction because of its amine chemistry and capacity to chelate iron.

5. Biological Stability. To evaluate oligonucleoside strand breakage which may occur in vivo as a result of nucleases or peptidases, the calf serum assay is used. Briefly, size fractionated oligomers are incubated in 50% fetal calf serum at 37° C. as a function of time. To analyze cleavage, the assay solution is analyzed by PAGE-SDS electrophoresis. Enzymatic cleavage is assessed from the fraction of polymer (F) which remains full length, assuming poison statistics: $F = \exp^n$, where n is the number of cleavages per oligomer induced by serum enzymes.

All publications mentioned in this specification are indicative of the level of skill of those skilled in the art to which the invention pertains. All publications are herein incorporated by reference to the same extent as if each individual publication was specifically and individually indicated to be incorporated by reference.

One skilled in the art will readily appreciate the present invention is well adapted to carry out the objects and obtain the ends and advantages mentioned, as well as those inherent therein. The compounds, methods, procedures and techniques described herein are presently representative of the preferred embodiments, are intended to be exemplary and not intended as limitations of the scope. Changes therein and other uses will occur to those skilled in the art which are encompassed within the spirit of the invention or defined by the scope of the appended claims.

What is claimed is:

1. A method of synthesizing a compound having the structure:

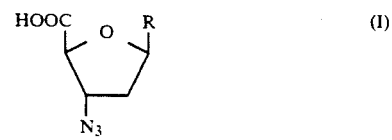

wherein R is a nucleo-base, comprising the step of oxidizing a 5'-hydroxymethyl functionality of a 3'-azido-2',3'-dideoxynucleoside or a 3'-azidodeoxynucleoside at ambient temperature in the presence of ruthenium tetraoxide.

2. The method of claim 1, wherein the ruthenium tetraoxide is generated in situ by treating $RuCl_3$ in an aqueous KOH solution with oxidizing agents selected from the group consisting of persulfate.

3. The method of claim 1, wherein the ruthenium tetraoxide is generated in situ by treating $RuCl_3$ in an aqueous KOH solution with $K_2S_2O_8$.

* * * * *

UNITED STATES PATENT AND TRADEMARK OFFICE
CERTIFICATE OF CORRECTION

PATENT NO. : 5,175,266
DATED : December 29, 1992
INVENTOR(S) : Rajender S. Varma, et. al.

It is certified that error appears in the above-indentified patent and that said Letters Patent is hereby corrected as shown below:

Column 1, line 32, change "oligonucleotidephosphorothioatesand" to -- oligonucleotide phosphorothioates and --.

Column 3, line 29, after "schematic" change "representation" to -- representations --.

Column 3, line 35, after "schematic" change "representation" to -- representations --.

Column 5, lines 24-25, delete extra spaces between "importance to" and "understanding."

Column 7, line 8, change "t-butyldimethylsilyl" to -- $\underline{t}$-butyldimethylsilyl --.

Column 8, line 30, before "-cyano" change "5," to -- 5' --.

Column 9, line 17, change "erythro" to -- <u>erythro</u> --.

Column 9, line 23, change "(s,3H,CH$_3$)" to -- (s,3H,C$\underline{H}_3$) --.

Column 9, line 24, change "(m,2H,2-H'&2-H")" to -- (m,2H,2-$\underline{H}$'&2-$\underline{H}$") --.

Column 9, line 25, change "4'H,3'H,&1'H" to -- 4'$\underline{H}$,3'$\underline{H}$,&1'$\underline{H}$ --.

Column 9, line 25, change "(s,1H,C$_6$-H)" to -- (s,1H,C$_6$-$\underline{H}$) --.

Column 9, line 43-44, change "erythropentofuranosyl" to --erythro-pentofuranosy

Column 9, lines 48-49, change "(s,3H,CH$_3$,2.2-2.5(m,2H,2'-H)" to -- (s,3H,C$\underline{H}_3$,2.2-2.5(m,2H,2'-$\underline{H}$) --.

UNITED STATES PATENT AND TRADEMARK OFFICE
CERTIFICATE OF CORRECTION

Page 2 of 4

PATENT NO. : 5,175,266
DATED : December 29, 1992
INVENTOR(S) : Rajender S. Varma, et. al.

It is certified that error appears in the above-indentified patent and that said Letters Patent is hereby corrected as shown below:

Column 9, line 49, change "(m,1H,3'-H)" to -- (m,1H,3'-H̲) --.

Column 9, line 50, change "CH₂NH" to -- CH̲₂NH --.

Column 9, line 51, change "(s,5H,C₆H₅)" to -- (s,5H,C₆H̲₅) --.

Column 9, line 53, change "(-C◯O's)" to -- (-C=O's) --.

Column 9, line 61, change "3-dideoxy-β-D-erythro-pentofuranosyl" to -- 3-dideoxy-β-D-erythro-pentofuranosyl --.

Column 10, line 1, change "(s,3H,CH₃)" to -- (s,3H,CH̲₃) --.

Column 10, line 2, change "(m,2H,2'H-2"H)" to -- (m,2H,2'H̲&2"H̲) --.

Column 10, line 3, change "(dd,1H,1'H)" to -- (dd,1H,1'H̲) --.

Column 10, line 4-5, change "(COOH - COHN)" to -- (COOH & COHN) --.

Column 10, line 22, change "β-D-erythro-pentofuranosyl-" to -- β-D-erythro-pentofuranosyl- --.

Column 10, line 30, change "(t,3H,CH₃)" to -- (t,3H,CH̲₃) --.

Column 10, lines 30-31, change "(s,3H,5-CH₃)" to -- (s,3H,5-CH̲₃) --.

Column 10, line 31, change "(m,2H,2'-H)" to -- (m,2H,2'-H̲) --.

Column 10, lines 31-32, change "(m,4H,C-H₂-CH₃,3'-H,4'-H)" to -- (m,4H,CH₂-CH₃,3'-H̲,4'-H̲) --.

UNITED STATES PATENT AND TRADEMARK OFFICE
CERTIFICATE OF CORRECTION

PATENT NO. : 5,175,266
DATED : December 29, 1992
INVENTOR(S) : Rajender S. Varma, et. al.

It is certified that error appears in the above-indentified patent and that said Letters Patent is hereby corrected as shown below:

Column 10, line 33, change "(s,1H,H-6)" to -- (s,1H,H-6) --.

Column 10, line 42, change "β-D-erythro-pentofuranosyl-" to -- β-D-erythro-pentofuranosyl- --.

Column 10, line 45, change "(s,3H,CH$_3$)" to -- (s,3H,CH$_3$) --.

Column 10, line 46, change "(m,2H,2'-H)" to -- (m,2H,2'-H) --.

Column 10, line 46, change "(m,1H,4'-H)" to -- (m,1H,4'-H) --.

Column 10, line 47, change "(m,1H,3'-H)" to -- (m,1H,3'-H) --.

Column 10, line 47, change "(br,NH$_2$)" to -- (br,NH$_2$) --.

Column 10, line 48, change "(d,J=6.6Hz,1H,1'-H)" to -- (d,J=6.6Hz,1H,1'-H) --.

Column 10, line 48, change "(s,1H,C$_6$-H)" to -- (s,1H,C$_6$-H) --.

Column 11, line 6, change "β-D-erythro-pentofuranosyl-" to -- β-D-erythro-pentofuranosyl- --.

Column 13, line 23, change "EXAMPLE 2" to -- EXAMPLE 12 --.

Column 14, line 41, change "t-butyldimethylsilyl" to -- t-butyldimethylsilyl --.

Column 14, line 46, change "β-D-erythro-pentofuranosyl-" to -- β-D-erythro-pentofuranosyl- --.

UNITED STATES PATENT AND TRADEMARK OFFICE
CERTIFICATE OF CORRECTION

PATENT NO.   : 5,175,266
DATED        : December 29, 1992
INVENTOR(S)  : Rajender S. Varma, et. al.

It is certified that error appears in the above-indentified patent and that said Letters Patent is hereby corrected as shown below:

Column 14, line 50-51, change "β-D-erythro-pentofuranosyl-" to -- β-$\underline{D}$-$\underline{erythro}$-

Column 14, line 65-66, change "β-D-erythro-pentofuranosyl-" to -- β-$\underline{D}$-$\underline{erythro}$-

Column 15, line 1-2 change "β-D-erythro-pentofuranosyl-" to -- β-$\underline{D}$-$\underline{erythro}$-

Column 15, line 6, change "β-D-erythro-pentofuranosyl-" to -- β-$\underline{D}$-$\underline{erythro}$-pentofuranosyl- --.

Column 17, line 23, after "occur" change "in vivo" to -- $\underline{in\ vivo}$ --.

Column 17, line 30, after "statistics:" change "F=exp$^m$" to -- F-exp$^n$ --.

Column 18, line 30, after "generated" change "in situ" to -- $\underline{in\ situ}$ --.

Column 18, line 34, after "generated" change "in situ" to -- $\underline{in\ situ}$ --.

Signed and Sealed this

Eleventh Day of October, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,175,266
DATED : December 29, 1992
INVENTOR(S) : Rajender S. Varma, et al.

It is certified that error appears in the above-identified patent and that said Letters Patent is hereby corrected as shown below:

Column 1, between lines 5 and 6, insert the following paragraph:

"STATEMENT REGARDING FEDERALLY SPONSORED RESEARCH OR DEVELOPMENT

Research leading to this invention was supported in part by a grant from the U.S. Government, through the National Institutes of Health. The U.S. Government has certain rights in this invention."

Signed and Sealed this

Eighteenth Day of March, 1997

Attest:

BRUCE LEHMAN

Attesting Officer

Commissioner of Patents and Trademarks